(12) United States Patent
Locht et al.

(10) Patent No.: US 7,833,699 B2
(45) Date of Patent: Nov. 16, 2010

(54) **DETECTION OF TUBERCULOSIS AND INFECTION BY *MYCOBACTERIUM TUBERCULOSIS* USING HBHA**

(75) Inventors: Camille Locht, Brussels (BE); Françoise Mascart, Brussels (BE); Stéphane Temmerman, Brussels (BE); Jean-Michel Hougardy, Itterbeek (BE); Sammy Place, Rebecq (BE); Christian Sergheraert, Morbecque (FR)

(73) Assignees: Institute Pasteur de Lille, Lille (FR); Inserm (Institut National de la Sante Et de la Recherche Medicale), Paris (FR); Universite Libre de Bruxelles, Bruxelles (BE); Universite du Droit Et de la Sante de Lille II, Lille (FR)

( * ) Notice: Subject to any disclaimer, the term of this patent is extended or adjusted under 35 U.S.C. 154(b) by 289 days.

(21) Appl. No.: 11/646,299

(22) Filed: Dec. 28, 2006

(65) Prior Publication Data
US 2007/0212740 A1    Sep. 13, 2007

Related U.S. Application Data

(63) Continuation of application No. PCT/EP2005/007902, filed on Jun. 30, 2005.

(30) Foreign Application Priority Data

Jun. 30, 2004  (FR) .................................. 04 07255

(51) Int. Cl.
*C12Q 1/00* (2006.01)
*A61K 39/38* (2006.01)
*A61K 39/04* (2006.01)

(52) U.S. Cl. ................ 435/4; 435/29; 435/41; 424/9.1; 424/9.2; 424/184.1; 424/248.1; 424/278.1; 530/300; 530/350

(58) Field of Classification Search ............. 435/4, 435/29, 41; 424/9.1, 9.2, 184.1, 248.1, 278.1; 530/300, 350
See application file for complete search history.

(56) References Cited

FOREIGN PATENT DOCUMENTS

| WO | WO-97/44463 A2 | 11/1997 |
|----|----------------|---------|
| WO | WO-02/054073 A2 | 7/2002 |

OTHER PUBLICATIONS

Masungi et al., Journal of Infectious Diseases, vol. 185, No. 4, Feb. 15, 2002, pp. 513-520.

*Primary Examiner*—Rodney P. Swartz
(74) *Attorney, Agent, or Firm*—Birch, Stewart, Kolasch & Birch, LLP.

(57) ABSTRACT

The present invention concerns methods for in vitro detection of an infection by *Mycobacterium tuberculosis* in mammals, and methods for in vitro distinction between mammals infected with *Mycobacterium tuberculosis* in which the disease is declared (active form) and mammals which are infected but asymptomatic for tuberculosis (latent form), and a method for in vitro distinction between mammals presenting an active form of tuberculosis and mammals not infected by *M. tuberculosis* or presenting a latent form of tuberculosis. The present invention also pertains to kits for detection and distinction between infected mammals presenting tuberculosis symptoms and infected mammals with no disease development, and a kit for distinguishing between mammals presenting an active form of tuberculosis and mammals not infected by *M. tuberculosis* or presenting a latent form of tuberculosis.

29 Claims, 15 Drawing Sheets

SEQUENCE LISTING

```
<160> NUMBER OF SEQ ID NOS: 1

<210> SEQ ID NO 1
<211> LENGTH: 39
<212> TYPE: PRT
<213> ORGANISM: Mycobacterium tuberculosis
<220> FEATURE:
<221> NAME/KEY: MISC_FEATURE
<222> LOCATION: (1)..(39)
<223> OTHER INFORMATION: Amino acids 161 to 199 of HBHA C-terminal
      fragment

<400> SEQUENCE: 1

Lys Lys Ala Ala Pro Ala Lys Lys Ala Ala Pro Ala Lys Lys Ala Ala
1               5                   10                  15

Pro Ala Lys Lys Ala Ala Ala Lys Lys Ala Pro Ala Lys Lys Ala Ala
            20                  25                  30

Ala Lys Lys Val Thr Gln Lys
        35
```

DETECTION OF TUBERCULOSIS AND INFECTION BY *MYCOBACTERIUM TUBERCULOSIS* USING HBHA

The present invention relates to methods for in vitro detection of infection with *Mycobacterium tuberculosis* in mammals and to methods for in vitro distinction between mammals infected with *Mycobacterium tuberculosis* for which the disease is declared (active form) and mammals infected but asymptomatic for tuberculosis (latent form), and to a method for in vitro distinction between mammals presenting an active form of tuberculosis and mammals not infected by *M. tuberculosis* or presenting a latent form of tuberculosis. The present invention also relates to kits for detecting and distinguishing between infected mammals presenting the symptoms of tuberculosis and infected mammals not having developed the disease, and to a kit for distinguishing between mammals presenting an active form of tuberculosis and mammals not infected by *M. tuberculosis* or presenting a latent form of tuberculosis.

Tuberculosis is a bacterial disease which primarily affects the lungs (pulmonary tuberculosis); other parts of the body may also be affected, such as the lymph node, the pleura (pleural space), the joints, the bones, the genito-urinary tract, the meninges, the peritoneum, the gastrointestinal tract, the central nervous system, the adrenal glands or the pericardium (extrapulmonary tuberculosis).

Tuberculosis is transmitted aerially, by exposure to germs present in the saliva and pulmonary expectorations (for example when coughing or sneezing) from a mammal carrying the disease or by contact with lesions. The symptoms of tuberculosis are fever, night sweats, fatigue, weight loss, loss of appetite and a persistent cough.

In 2004, tuberculosis still represented a major public health problem as it is responsible for more than two million deaths per year worldwide and a third of the worldwide population is infected by the responsible agent, *Mycobacterium tuberculosis*, routinely known as Koch's bacillus or KB. Tuberculosis is thus the second largest cause of death by infectious disease, just behind infection by the human immunodeficiency virus (1). For this reason, both the World Health Organization and the European Community have made research in this field one of their priorities. Three main objectives have been defined:
a) prevention by developing a vaccine which will provide better protection than the current vaccine, BCG (Bacillus of Calmette and Guérin);
b) improving means for rapid diagnosis of tuberculosis; and
c) discovering faster treatments facilitating administration and thus avoiding the development of multi-resistant bacterial strains.

Inadequate detection of new cases of tuberculosis has been identified as a major reason for the worldwide increase in the number of cases of tuberculosis (2). Microscopic examination and the culture of sputum are recognized as two good routes to diagnosing pulmonary tuberculosis. However, the results of mycobacterial cultures can only be interpreted after 6 to 8 weeks, and developing countries do not always have access to the infrastructure required for this technique, which greatly limits the utility of culturing as a diagnostic test of the first intention (3). The determination of acido-resistant bacillae in sputum thus remains the most useful test for rapid diagnosis of pulmonary tuberculosis, but identification is unfortunately only positive in 50% to 60% of cases of pulmonary tuberculosis, partly due to the fact that 5000 to 10000 bacillae per µl of sputum are required for the test to be positive (3). Diagnosing pulmonary tuberculosis is even more difficult in a child who, when young, rarely expectorates, and from whom a gastric aspiration is usually collected. However, direct examination of such samples is positive in less than 20% of children with proven tuberculosis, which is much lower than the results obtained in the adults (4). Finally, a diagnosis of extra pulmonary tuberculosis, which is more frequent in children than in adults, is still difficult to make. It is often primarily based on the anatomo-pathological examination of biopsies. The conventional histological appearance of tuberculosis is the presence of granulomae with caseous necrosis. The granuloma is constituted by histiocytes, epitheliodal cells and/or giant Langerhans type cells. However, both for lymphatic ganglia and for pulmonary samples, a certain number of different diagnoses can be interpreted as infections (non tuberculous mycobacteria, mycosis, etc) or non-infectious diseases (sarcoidosis, Wegener's disease, etc) (5). To validate the diagnosis of tuberculosis, a histological examination must be completed by the carrying out of special stains, such as Ziehl-Nielsen stain which exploits the alcohol-acidoresistant properties of *Mycobacterium tuberculosis*. However, a quantity of $10^6$ organisms per millimeter of tissue is necessary to obtain a positive Ziehl-Nielsen stain (6).

Finally, a diagnosis is still often based on a set of clinical or radiological data and on the results of a skin test for delayed hypersensitivity to tuberculin (purified protein derivative or PPD). This last test cannot, however, readily differentiate individuals infected with *M. tuberculosis* from those vaccinated with BCG, and cross reactions with environmental mycobacteria render its specificity poor. That test, which is based on the demonstration of a cellular immune response, also has poor sensitivity in immunodeficient individuals. Finally, though it enables to identify persons infected with *M. tuberculosis* in a population of unvaccinated individuals, it unfortunately cannot differentiate individuals presenting a latent tuberculosis (symptom-free) from those with an active disease. In fact, only 5% to 10% of individuals infected with *M. tuberculosis* develop a disease, while the others are protected against the disease even if they are infected (7). The practical use of that test, then, is extremely limited.

More recently, molecular biological techniques have been developed to demonstrate the presence of *M. tuberculosis* using PCR (polymerase chain reaction) techniques. Such techniques are sensitive (95%), but this is especially true for sputum samples for which direct examination is positive. In contrast, their specificity is excellent (98%), which allows *M. tuberculosis* to be distinguished from other mycobacteria. However, the technique is expensive, limiting its application.

It thus appears to be a matter of urgency to develop novel means for rapidly diagnosing tuberculosis. One of the possible approaches consists of exploiting the differences in immune responses which may exist between uninfected subjects and infected individuals depending on whether or not they are diseased. Different tests, which are based on a study of the induced secretion of IFN-γ in circulating lymphocytes by mycobacterial antigens, have thus been reported in the literature (8). An analysis of IFN-γ secretion induced by tuberculin, a complex mixture of mycobacterial antigens, however, has the same limitations as its use for skin tests. In fact, all sensitized individuals, whether diseased or not, and persons sensitized to the antigens present in certain atypical mycobacteria or simply in BCG will respond. The advantage of that test over skin tests is that an analysis of the lymphocyte response in parallel with a positive control (phytohaemagglutinin) can detect patients who do not respond to PPD because of severe immunodeficiency. Specific antigens for *M. tuberculosis* were then isolated and used in in vitro IFN-γ secretion tests and the specificity of said tests were clearly far superior.

Essentially, the antigens ESAT-6 and CFP10 may be used, but it should be pointed out that the discrimination obtained by those antigens between diseased or healthy, infected subjects is still far from perfect (9).

A study of immune responses in humans concerning "heparin binding haemagglutin" (HBHA) shows excellent discrimination between diseased and healthy, infected persons. HBHA is an adhesion, expressed on the surface of bacteria forming part of the *Mycobacterium* complex, and not on the surface of non-pathogenic bacteria such as *M. smegniatis* (10). This protein is secreted by *M. tuberculosis* and is responsible for dissemination of the infection (11). HBHA has a methylated C-terminal region and expresses at the surface, while the non-methylated N-terminal portion anchors the adhesin in the mycobacterial wall (12). Methylation is important, not only to induce immune responses in humans, but also to induce a protective immune response in the mouse (13). It has been shown that the induced secretion of IFN-γ in circulating lymphocytes by in vitro HBHA stimulation differs depending on whether the persons infected with *M. tuberculosis* were diseased or not (14). While IFN-γ is secreted by the peripheral lymphocytes in the majority of healthy patients in response to HBHA, only a minority of tuberculous patients responded to that antigen by secreting IFN-γ. However, discrimination between these two groups of individuals on the basis of these preliminary results was insufficient for conducting a diagnostic test.

The present invention aims to provide methods for in vitro detection of *Mycobacterium tuberculosis* infection in mammals.

The present invention also aims to provide methods for in vitro distinction between mammals infected with *Mycobacterium tuberculosis* in which the disease is declared and mammals infected but not developing tuberculosis, to a method for in vitro identification of latent TB patients within a healthy population and to a method for in vitro distinction between mammals presenting an active form of tuberculosis and mammals not infected by *M. tuberculosis* or presenting a latent form of tuberculosis.

Finally, the invention also aims to provide kits which contain all of the elements necessary for detecting *Mycobacterium tuberculosis* infection and which can distinguish infected patients who express the disease (active tuberculosis) from infected and asymptomatic patients (latent tuberculosis), and a kit for distinguishing between mammals presenting an active form of tuberculosis and mammals not infected by *M. tuberculosis* or presenting a latent form of tuberculosis.

The invention also pertains to the use of HBHA in its native or recombinant form in a test for detecting infection by *Mycobacterium tuberculosis* and for distinguishing between patients presenting a latent form of tuberculosis and patients presenting all of the symptoms of tuberculosis and being diseased. These and other aims are embodied in the present invention, as will be demonstrated in the summary of the invention, the description and the preferred implementations as well as the claims.

SUMMARY OF THE INVENTION

The present invention describes an in vitro method for detecting and differentiating between a mammal presenting a latent tuberculosis and a mammal presenting an active tuberculosis, said method comprising a) obtaining a biological sample from said mammal; b) measuring the quantity of antibodies (IgG) directed against two distinct forms of the HBHA protein, and contained in said biological sample; and c) comparing the titers of antibody obtained for the two forms of the HBHA protein, in which the comparison of the antibody titers obtained for the two distinct forms in the mammal presenting a latent tuberculosis is different from that obtained in the mammal presenting an active tuberculosis.

The scope of the invention also encompasses a kit for detecting and differentiating between a mammal presenting a latent tuberculosis and a mammal presenting an active tuberculosis, said kit comprising two distinct forms of HBHA selected from the group consisting of a) native HBHA and recombinant HBHA, or b) the rHBHAΔC fragment and the methylated C-terminal fragment of HBHA, the reagents required to constitute a medium for carrying out the immunological reaction between the antibodies contained in the biological sample from said mammal and the distinct forms of HBHA, and the reagents allowing detection of immunological complexes formed during said immunological reaction.

The invention also concerns an in vitro method for detecting and differentiating between a mammal presenting a latent tuberculosis and a mammal presenting an active tuberculosis, or for identifying a mammal presenting a latent tuberculosis within a healthy population, said method comprising a) obtaining a biological sample from said mammal; b) bringing said biological sample into contact, in an independent manner, with the native form of HBHA and with ESAT-6; c) measuring the HBHA-specific IFN-γ secretion and the ESAT-6-specific IFN-γ secretion; and d) calculating the ratio between the HBHA-specific IFN-γ secretion and the ESAT-6 specific IFN-γ secretion, in which said ratio obtained in a mammal presenting a latent tuberculosis is higher than the ratio obtained in a mammal presenting an active tuberculosis or obtained in a mammal not infected by *M. tuberculosis*.

The invention also pertains to a kit for detecting and differentiating between a mammal presenting a latent tuberculosis from a mammal presenting an active tuberculosis or for identifying a mammal presenting a latent tuberculosis within a healthy population, said kit comprising the native form of HBHA and ESAT-6, the reagents required to constitute a medium for carrying out contact, in an independent manner, of cells present in the biological sample from said mammal with native HBHA and ESAT-6 and reagents for detecting IFN-γ secretion following contact.

The invention also pertains to an in vitro method for detecting and differentiating between a mammal presenting an active tuberculosis and a mammal not infected by *M. tuberculosis* or a latent tuberculosis, said method comprising a) obtaining a biological sample from local infection sites of said mammal; b) bringing said biological sample into contact with the native or recombinant form of HBHA; and c) measuring the effect of said contact on HBHA-specific IFN-γ, in which the effect of the HBHA-specific IFN-γ is greater in a mammal presenting an active tuberculosis than in a mammal not infected by *M. tuberculosis* or presenting a latent tuberculosis.

The invention also defines a kit for detecting and differentiating between a mammal presenting an active tuberculosis from a mammal not infected by *M. tuberculosis* or presenting a latent tuberculosis, said kit comprising the native or recombinant form of HBHA, the reagents required to constitute a medium suitable for carrying out contact of the cells present in the biological sample from said mammal with HBHA, and the reagents allowing the detection of IFN-γ, following contact.

No significant difference was observed between these two populations p>0.05).

FIG. 2 compares titers of nHBHA-specific IgG versus rHBHA-specific IgG in tuberculous patients (TB) and subjects presenting a latent form of tuberculosis (PI).

Figure 2A:
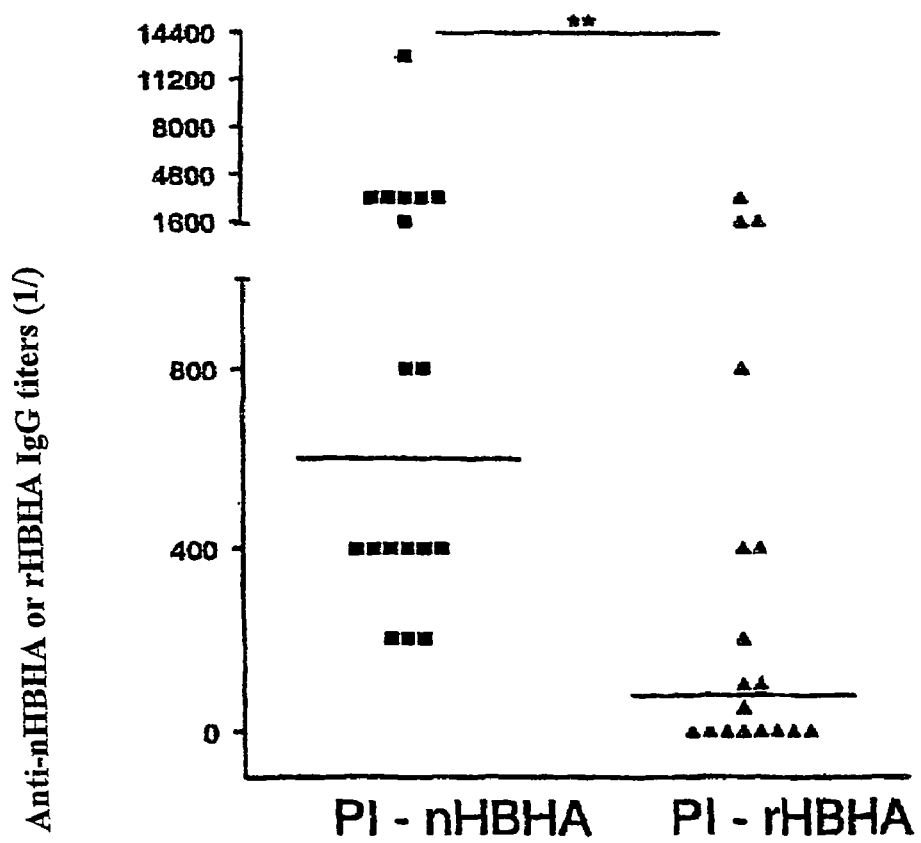

FIG. 2A shows that in subjects presenting a latent tuberculosis, the IgG recognize the native methylated form of HBHA better than the recombinant form (rHBHA) (p=0.0015), while in tuberculous patients (FIG. 2B), this difference is not significant (p>0.05).

FIG. 3 compares the titers of rHBHAΔC-specific IgG versus fragment C of HBHA (C-peptide)-specific IgG in tuberculous patients (TB) and in subjects presenting a latent form of tuberculosis (PI).

Figure 3A:
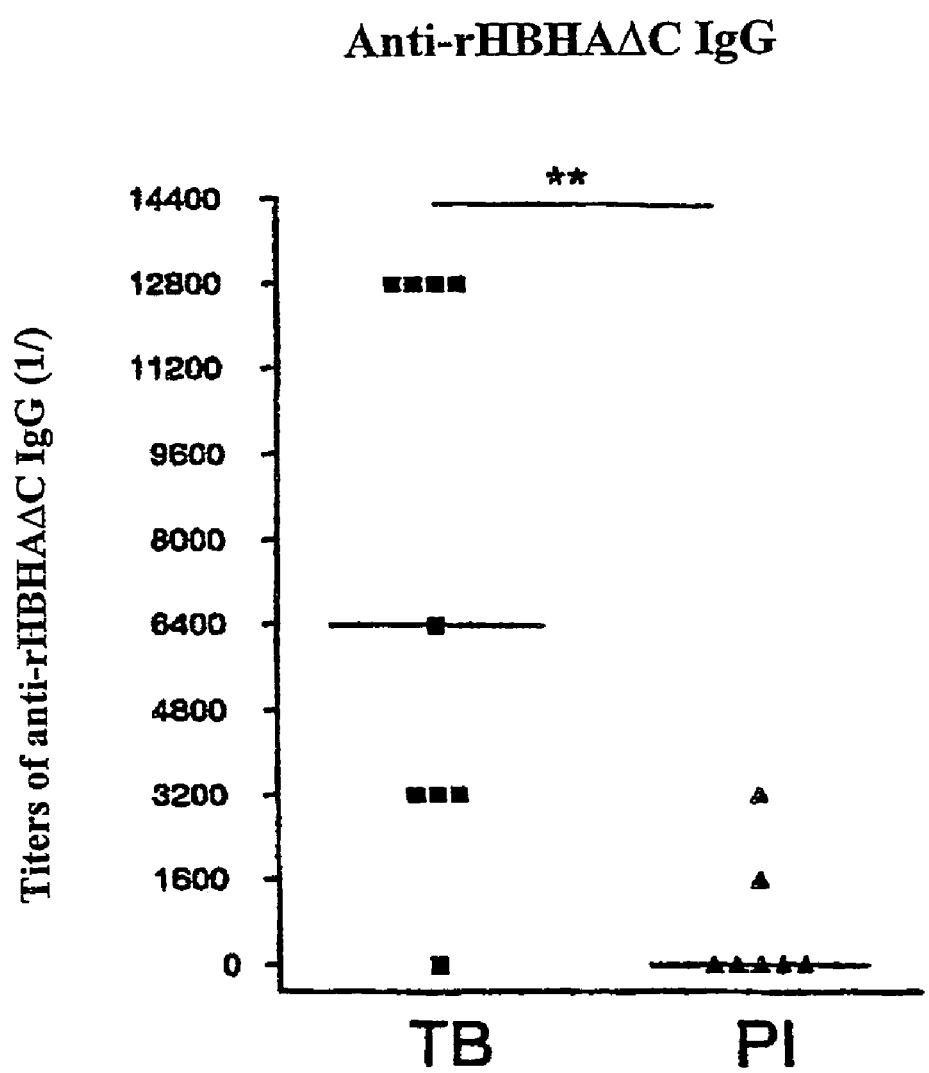

FIG. 3A shows that tuberculous patients have IgG which preferentially recognize the truncated recombinant form (rHBHAΔC) while the IgG of subjects presenting a latent tuberculosis barely recognize this form (p=0.0052). In contrast, in FIG. 3B, the IgG from tuberculous patients do not recognize the C-peptide fragment in contrast to subjects presenting a latent tuberculosis (p=0.0478).

Figure 4:
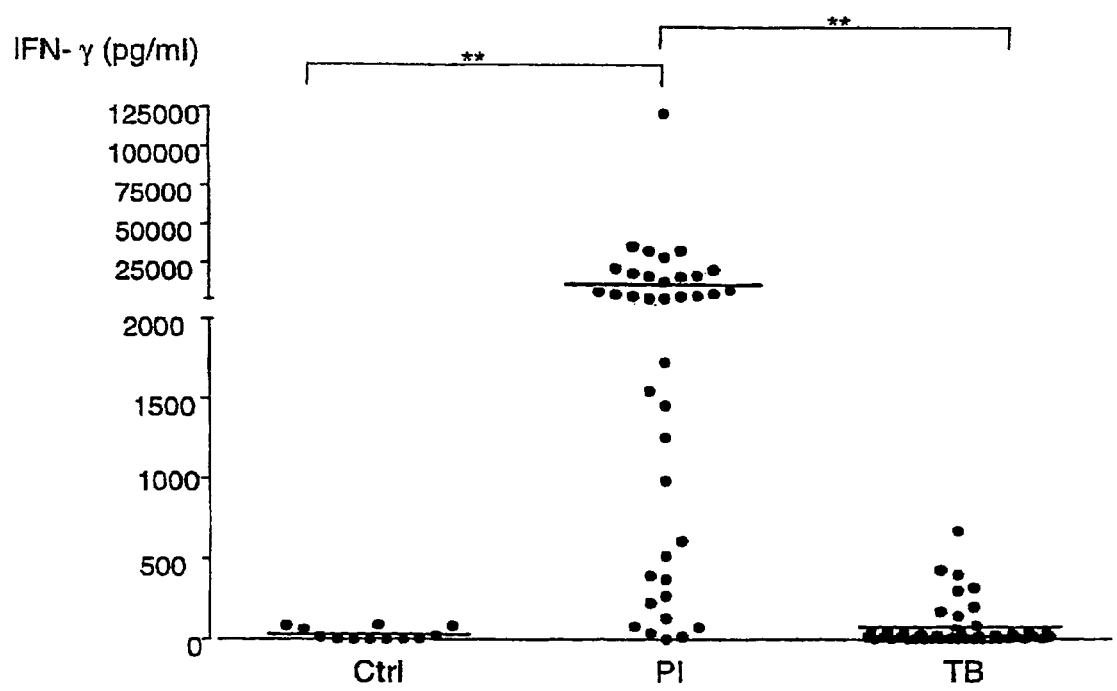

FIG. 4 shows FN-γ secretion in response to nHBHA in control subjects (ctrl; n=12), in subjects presenting a recent latent tuberculosis (<5 years) (PI; n=38) and in tuberculous patients (TB; n=46). The medians are respectively at 10 pg/ml, 2040 pg/ml and 16 pg/ml.**p<0.001.

Figure 5:
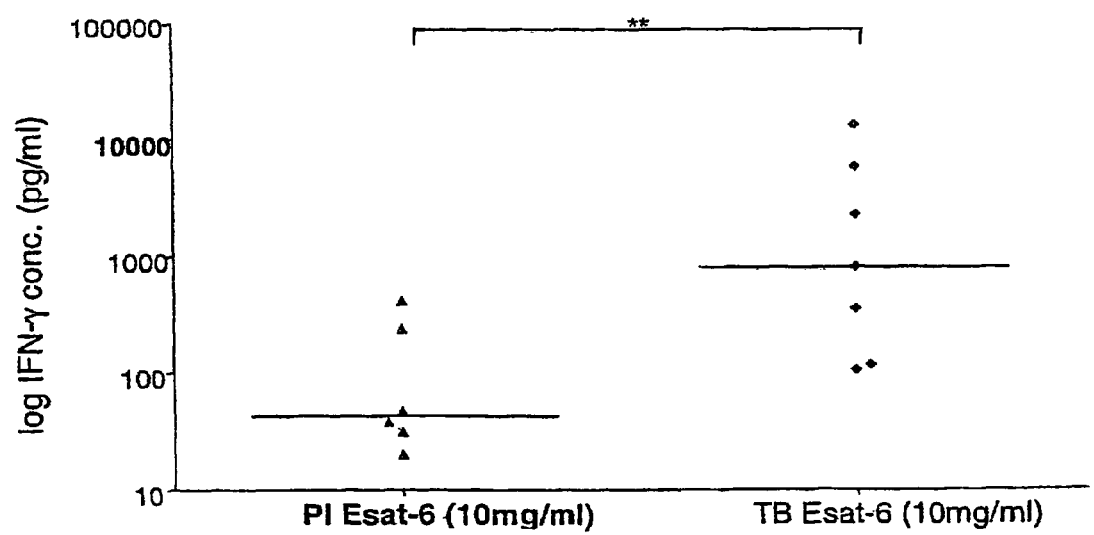

FIG. 5 shows the secretion of IFN-γ in response to ESAT-6 in subjects with a latent tuberculosis (PI) and tuberculous patients (TB).

In subjects presenting a latent tuberculosis, specific ESAT-6-induced IFN-γ secretion is significantly lower than that induced in tuberculous patients. The medians are at 42.50 pg/ml of IFN-γ for ESAT-6 in PI patients and 4072 pg/ml of IFN-γ in TB patients (p=0.02).

Figure 6:
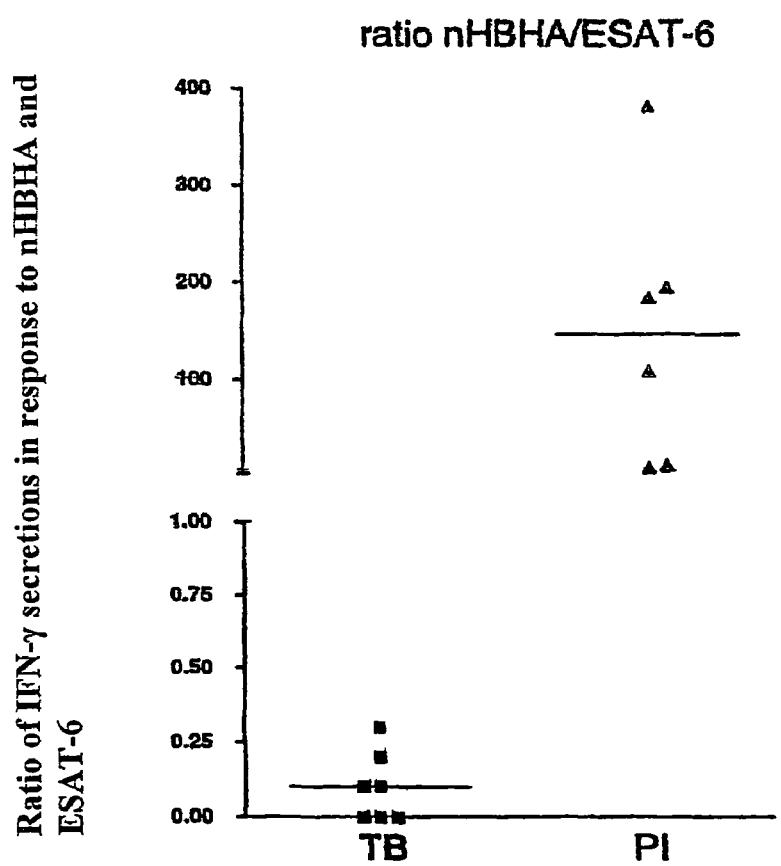

FIG. 6 shows the nHBHA/ESAT-6 ratio in tuberculosis patients and subjects presenting a latent tuberculosis. The medians are respectively 0.1 pg/ml and 146.2 pg/ml. This ratio is substantially in favour of subjects presenting a latent tuberculosis (p=0.001) and offers good discrimination between diseased infected subjects and those infected non-diseased (symptoms free).

Figure 7:
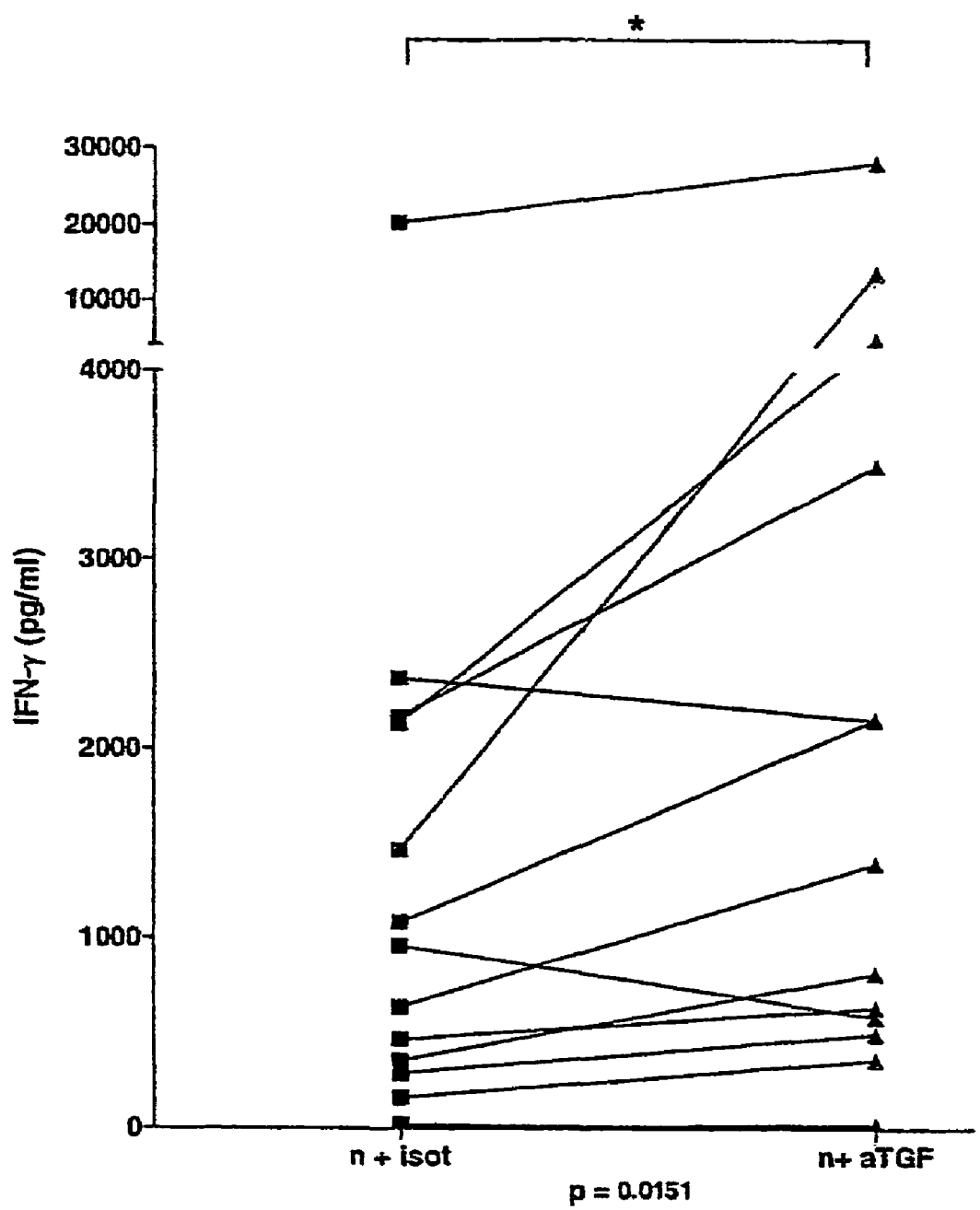

FIG. 7 shows the effect of anti-transforming growth factor beta 1, 2, 3 (anti-TGFβ) blocking antibodies on IFN-γ secretion in response to nHBHA by peripheral blood mononuclear cells (PBMC) in tuberculous patients. The IFN-γ was assayed in culture supernatants. Pair test (Wilcoxon—p=0.0161; n=15 pairs).

Figure 8:
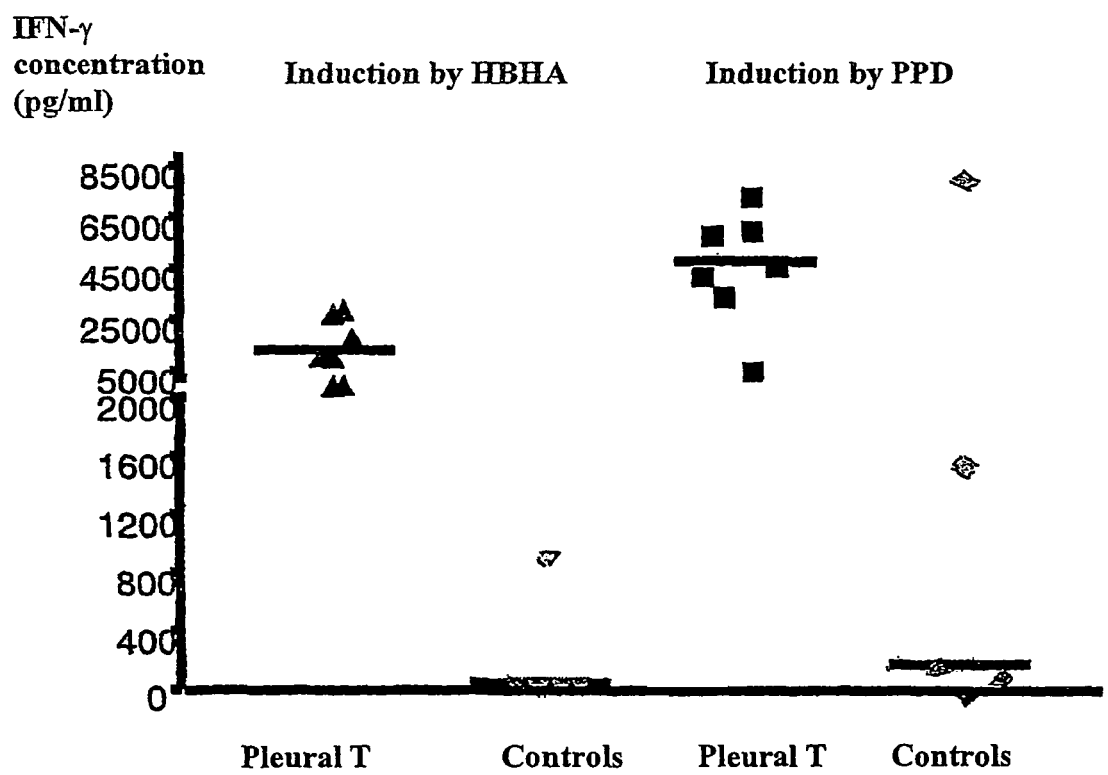

FIG. 8 shows a comparison between FN-γ secretion in response to nHBHA and to PPD by pleural fluid mononuclear cells removed from patients presenting a pleural effusion of tuberculous origin or of another origin. The IFN-γ was assayed in culture supernatants. The horizontal lines represent the medians.

Figure 9:
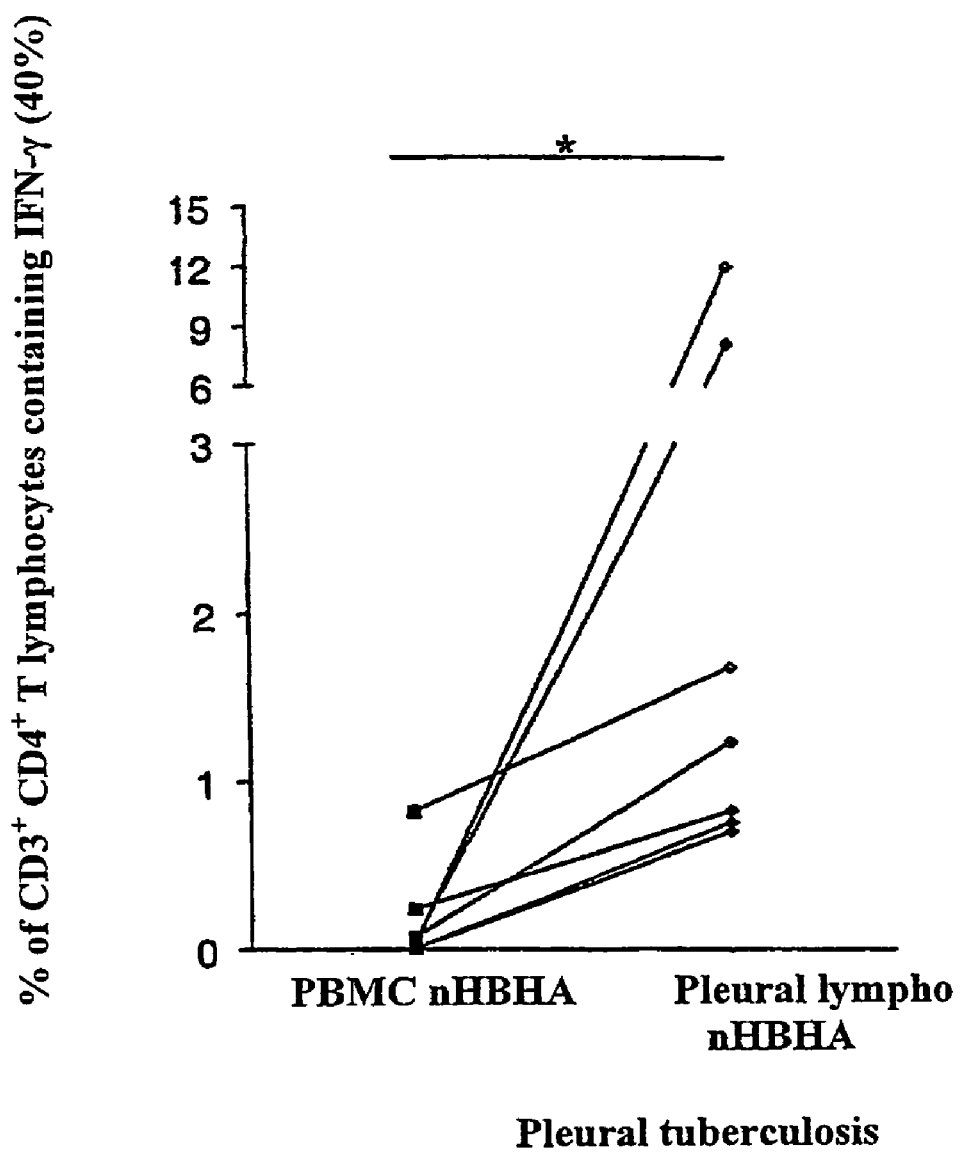

FIG. 9 illustrates the proportion of CD3$^+$CD4$^+$ T lymphocytes from PBMC (PBMC nHBHA) compared with pleural CD3$^+$CD4$^+$ T lymphocytes (Lympho. Pleural nHBHA) and containing intracytoplasmic IFN-γ in response to nHBHA, expressed as a percentage of cells expressing IFN-γ after stimulation by HBHA for 16 hours less the percentage of cells producing IFN-γ without stimulation by HBHA in tuberculous patients (n=7). The medians are respectively located at 0.04% and 1.23% (p=0.0156; Wilcoxon).

Figure 10:
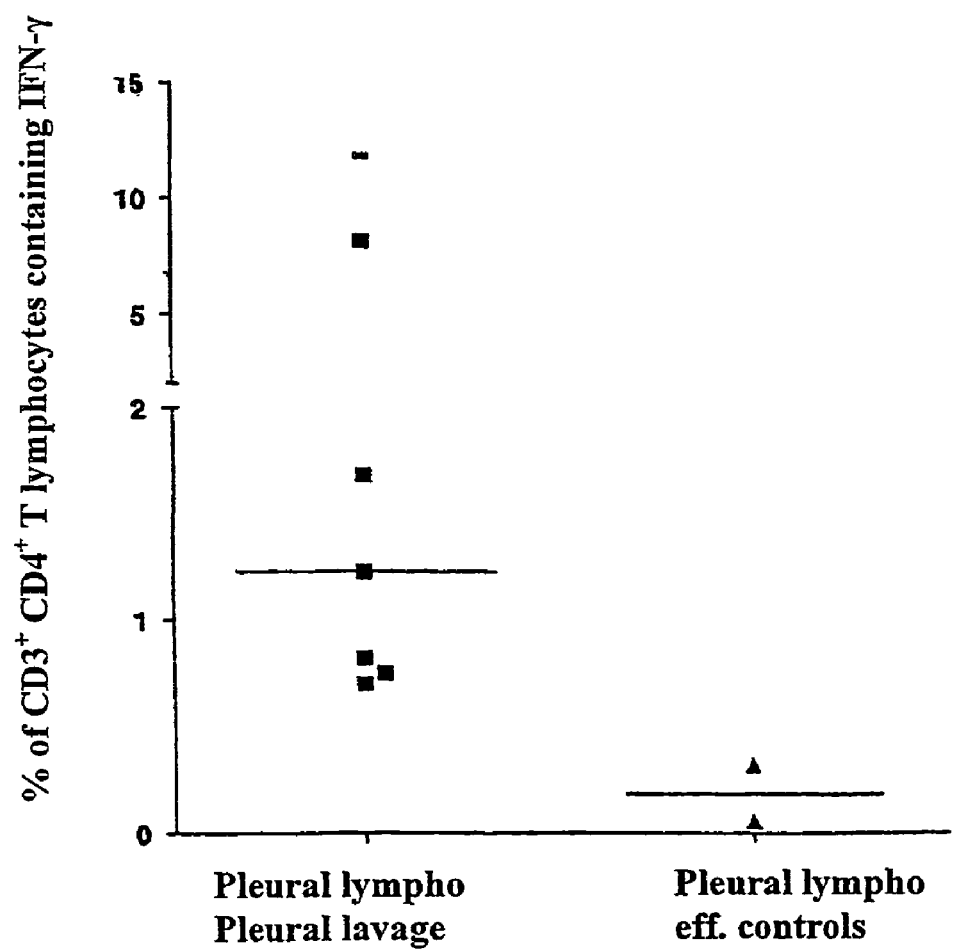

FIG. 10 represents the proportion of CD3$^+$CD4$^+$ T lymphocytes containing intracytoplasmic IFN-γ in response to nHBHA in the case of pleural tuberculosis (n=7; median=1.23%) and in the case of pleural effusions of non tuberculous origin (n=2; median=0.18%).

Figure 11A:
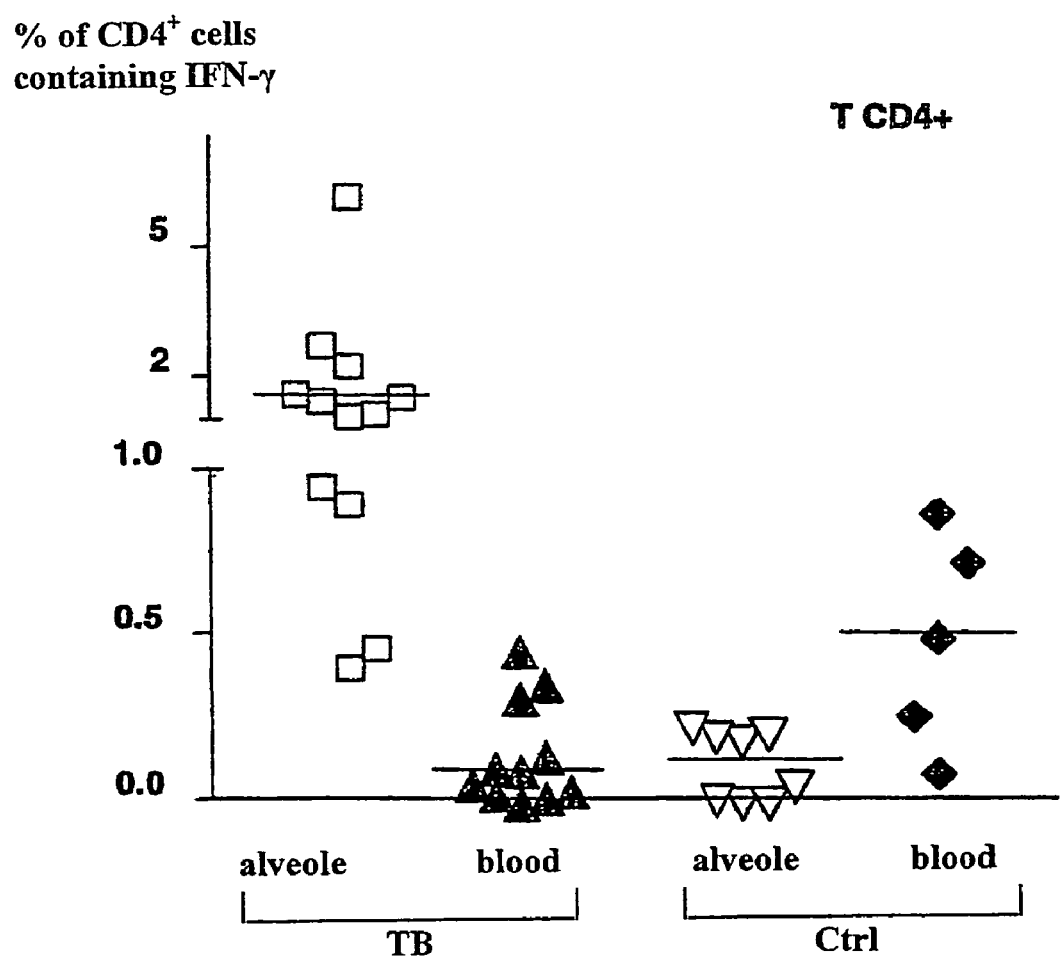
Figure 11B:
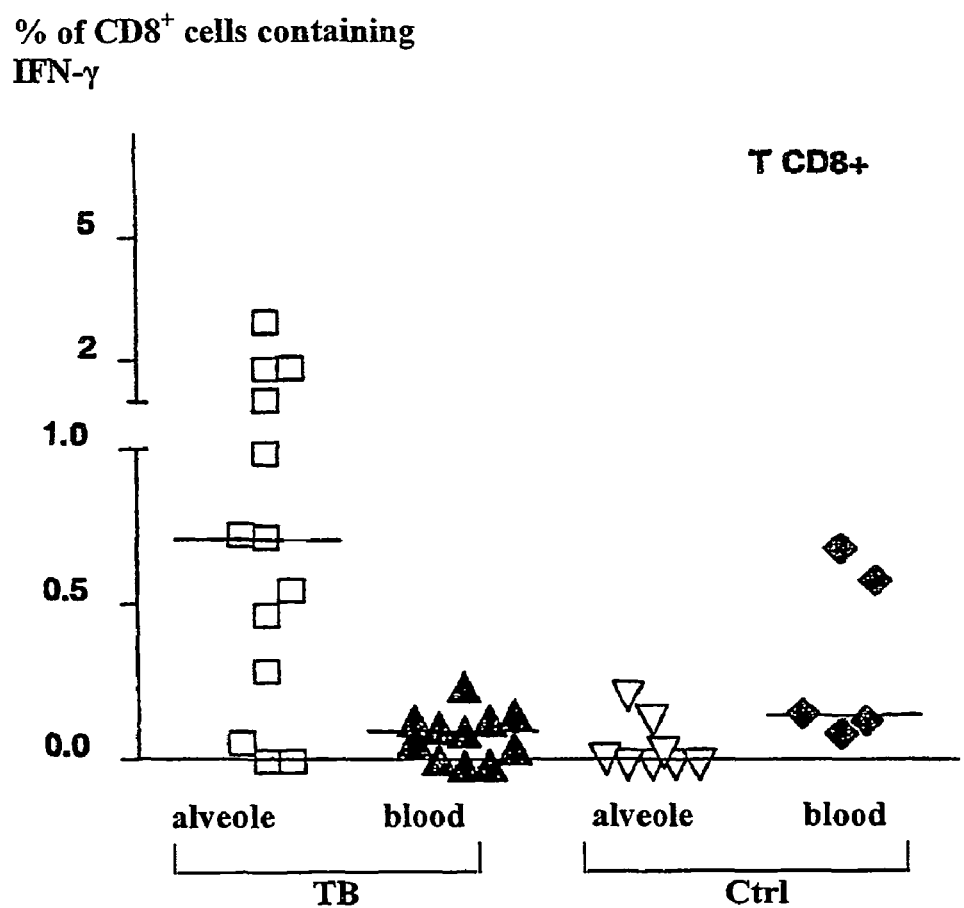

FIG. 11 shows the proportion of CD3$^+$CD4$^+$ (FIG. 11A) and of CD3$^+$CD8$^+$ (FIG. 11B) T lymphocytes containing IFN-γ in response to stimulation by nHBHA.

The figure shows alveolar lymphocyte cells (alveole) from broncho-alveolar lavage fluid or peripheral blood mononuclear cells (blood).

The broncho-alveolar lavage fluid was obtained either from patients presenting a pulmonary tuberculosis (TB) or from control subjects presenting a pulmonary lesion of non tuberculosis origin.

Figure 12:
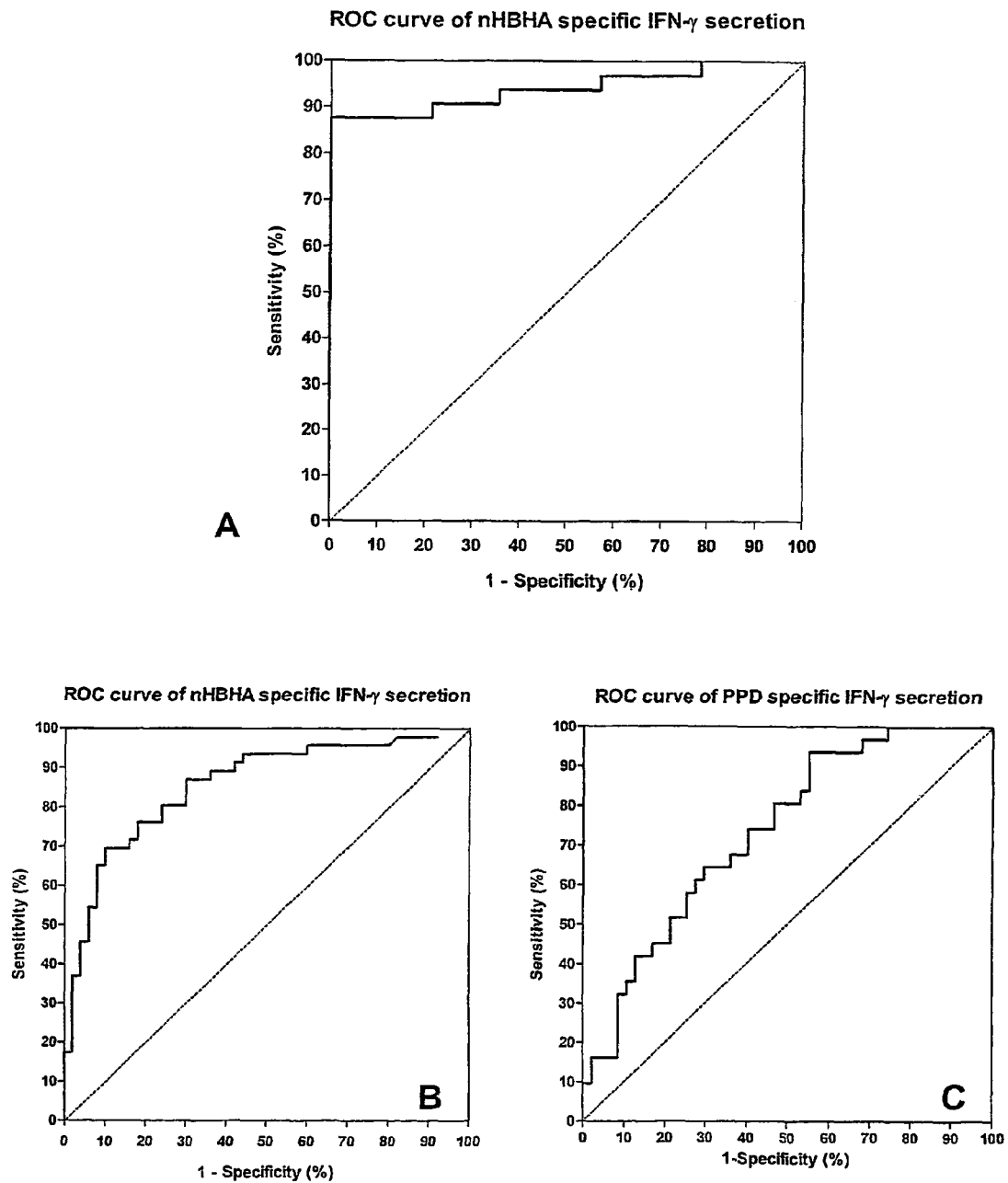

FIG. 12 shows ROC curves enabling discrimination between latent TB patients and control individuals from nHBHA-specific IFN-γ secretion (A), discrimination between latent TB and active TB patients from nHBHA-specific IFN-γ secretion (B) and discrimination between latent TB and active TB from PPD-specific IFN-γ secretion (C).

Regarding the figures described above, NS indicates that the differences are not significant, * indicates that the differences are significant with 0.01<p<0.05, and ** indicates that the differences are strongly significant, with p<0.01.

DESCRIPTION OF PREFERRED EMBODIMENTS

Within the context of the present invention, the term "mammal" designates any warm blooded animal covered with hair or fur, which suckles its young and bears live young. The term "mammal" includes but is not limited to humans, elephants, pigs, dogs, cats, cattle, cervidae, monkeys, etc.

While *Mycobacterium tuberculosis* principally infects a human host, other mammals may also be affected by this bacterial disease. In this case, infection with tuberculosis in mammals other than man is known as "inverse zoonosis" since *Mycobacterium tuberculosis* may be transmitted from man to an animal.

The abbreviation "HBHA" means "heparin binding haemagglutinin adhesin" and is a surface protein involved in adhesion to epithelial cells (Genbank accession numbers AF074390 and AAC26052.1). Identification of the HBHA protein in its native form has been described by Menzozzi et al (J Exp Med 184; 993-1001 (1996)). HBHA is a 199 amino acid protein the C terminal portion of which, is rich in lysine repetitions and contains the heparin binding site. This protein is required for extrapulmonary dissemination of *Mycobacterium tuberculosis* (Pethe et al, Nature 412: 190-194 (2001)).

Recombinant HBHA (rHBHA) is described in French patent application FR-A-01/14953 which reports that, in contrast to native HBHA protein (nHBHA), recombinant HBHA protein is not methylated on its lysine residues in the C terminal portion.

The rHBHAΔC fragment is described in Pethe et al (2000, Journal of Biological Chemistry 275 (19): 14273-14280). This fragment is derived from recombinant HBHA, for which amino acids 161-199 have been deleted.

The methylated C terminal fragment comprises amino acids 161 to 199 with the following sequence:

(SEQ ID NO: 1)
KKAAPAKKAAPAKKAAPAKKAAAKKAPAKKAAAKKVTQK

All of the references cited above are hereby incorporated by reference.

Within the context of the present invention, the abbreviation "PBMC" means "peripheral blood mononuclear cells". The PBMCs described here may be obtained by any method known in the literature. In one implementation of the invention, PBMCs are obtained by density gradient centrifuging from venous blood samples using a solution of about 9.1% (w/v) of sodium diatriazoate and a solution of about 5.7% of polysaccharide. This solution has a density of about 1.077±0.001 g/ml and an osmolality of 280±15 mOsm. This solution has the trade name Lymphoprep™.

The terms "latent tuberculosis" or "latent *Mycobacterium tuberculosis*" or "latent form of tuberculosis" are used interchangeably in the present application and mean that the mammal is infected by the bacterium of the *Mycobacterium tuberculosis* complex but is asymptomatic, i.e., develops no symptoms of tuberculosis. Further, the infected mammal cannot propagate tuberculosis to other mammals since no tuberculosis germs are present in the sputum. In other words, the mammal is infected but does not develop the disease.

The various forms of tuberculosis are classified as follows:

TB0: no exposure to the tuberculosis agent; no infection;

TB1: exposure to *Mycobacterium tuberculosis*, unknown degree of infection;

TB2: infection by tuberculosis agent, no symptom development (positive reaction to tuberculin skin test: positive PPD);

TB3: active form of tuberculosis, complete diagnosis;

TB4: clinically inactive form of tuberculosis, treated suitably or in remission; and TBS: possible tuberculosis, diagnosis in train ("rule out" TB).

The expression "healthy population" within the context of the invention refers to individuals who do not develop tuberculosis symptoms, whatever their infection status, i.e., not infected (TB0) or infected but healthy (latent tuberculosis; TB2).

The methods and kits described in the context of the present invention can distinguish the TB3 form from the TB2 form, the TB2 form from the TB0 form and the TB3 form from the TB0 form in the above classification.

The abbreviation PPD means "tuberculin protein-purified derivative". Tuberculosis is usually diagnosed by a test which involves intracutaneous exposure to PPD. This test is considered to be positive for tuberculosis if the skin reaction at the PPD exposure point is over a certain size, for example 10 mm or more.

The term "biological sample" as defined here encompasses respiratory and non respiratory samples. "Respiratory samples" includes bronchial aspirations, broncho-alveolar lavages (BAL), gastric lavage and sputum. Examples of non respiratory samples which may be used in the methods of the present invention include samples of effusion fluids such as pleural, abdominal and articular fluids, cerebrospinal fluids, cephalorachidian fluids, synovial fluids, peritoneal fluids, pericardiac fluids and other body fluids, lymph node, transbronchial, pleural and hepatic biopsies, medullary and lumbar punctures, urine or blood samples (PBMC or peripheral blood mononuclear cells), pus aspirations, etc.

The term "from the infection site" encompasses any biological sample removed from a tuberculosis infection site and encompasses any of the biological samples mentioned above, and others.

The methods of the present invention can on the one hand detect in vitro an immune response, in the infected mammal, to the HBHA protein of *Mycobacterium tuberculosis*, a sign of infection by said pathogenic agent, and on the other hand distinguish in vitro, optionally complementary to existing diagnostic methods, the latent form from the active form of tuberculosis, in other words the non-infectious from the infectious forms respectively.

The present invention concerns an in vitro method for detecting and differentiating between a mammal presenting a latent tuberculosis and a mammal presenting an active tuberculosis, said method comprising a) obtaining a biological sample from said mammal;

b) measuring the quantity of antibodies (IgG) directed against two distinct forms of the HBHA protein, and contained in said biological sample, under suitable conditions for the formation of the antibody-HBHA interaction; and c) comparing the titers of antibody obtained for the two forms of the HBHA protein, in which the comparison of the antibody titers obtained for the two distinct forms in the mammal presenting a latent tuberculosis is different from that obtained in the mammal presenting an active tuberculosis.

Starting from a biological sample from a mammal and using the characteristics of the immune responses directed against the HBHA protein of *Mycobacterium tuberculosis*, which are specific to the different forms of tuberculosis (active versus latent), this method can distinguish between infected mammals those who are diseased and those which are not. Thus, mammals presenting a latent form of tuberculosis and those presenting an active form of tuberculosis have immune responses, in particular a humoral response, which differ with respect to the HBHA protein.

Antibodies such as immunoglobulins G (IgG) deriving from mammals presenting a latent form of tuberculosis and those presenting an active form of tuberculosis recognize distinct portions of the HBHA protein. It is thus possible to modulate the structure of the HBHA protein to obtain distinct forms of HBHA and distinguish the different forms of tuberculosis. The term "distinct form of HBHA" means any modification to the structure of the HBHA protein with respect to the number (deletion or addition) and/or the nature (substitution of amino acids, with different or identical size, charge, steric hindrance) of its amino acids residues, and/or any post-translational modification such as acetylation, amidation, biotinylation, carboxylation, hydroxylation, methylation, phosphorylation or sulphatation or by adding lipids (isoprenylation, palmitoylation and myristoylation), glucides (glycosylation) or polypeptides (ubiquitination). In the context of the invention, the two forms are termed distinct when they are recognized in different manners by antibodies from mammals presenting a latent form and antibodies from mammals presenting an active form of tuberculosis.

Titration, i.e., determining the quantity of antibodies (serological assays) recognizing each form of HBHA is carried out in an independent manner, using any technique which is known to the skilled person, such as direct or indirect ELISA, (enzyme linked immunosorbant assay) or by radioimmunoassay (RIA), allowing contact of the antibodies contained in the biological sample with the distinct forms of HBHA. "In an independent manner" means that a portion of the sample is brought into contact with one form of the HBHA protein and another portion of the sample is brought into contact with a second form of the HBHA protein. Contact between the antibodies present in the sample and the forms of HBHA allowing their interaction and the detection of said interaction is carried out under appropriate conditions which are known to the skilled person. Thus, as an example, the following may be modified: the technique for coupling the antigen (HBHA) to the support, the biological sample dilutions, the concentrations of the distinct forms of HBHA, the temperature and the contact period and if needed the nature and concentration of secondary antibodies, as well as the parameters allowing detection of interaction, such as a reduction in the background noise, the choice of labeling (radioactivity, fluorochrome), or the acquisition time for the detection signal.

As an example of an ELISA protocol, the distinct forms of HBHA are diluted in a suitable buffer (coating) in a concentration in the range 1 to 10 µg/ml and incubated (50 to 200 µl) in microplate wells for 1 to 6 hours at room temperature (RT) or overnight at 4° C. Commonly used buffered solutions are 50 mM sodium carbonate, pH 6.9; 20 mM Tris-HCl, pH 8.5 or 10 mM PBS, pH 7.2-7.4. The plate is then washed with a washing solution (200 to 300 µl) comprising 0.1 M PBS or TBS, pH 7.4, with a detergent such as Triton or Tween 20 (0.01% to 0.05% final concentration). A saturation solution (200 to 300 µl) such as PBS containing skimmed milk powder, casein or gelatin, is then applied to block non specific interactions, for 30 to 60 minutes at 37° C. or at room temperature, then the excess is eliminated after several washes. The diluted ($1/10^{th}$ to $1/1000^{th}$) biological sample (100 to 200 µl) is incubated for 30 minutes to 2 hours at 37° C. or at room temperature, or overnight at 4° C., followed by several washes. The secondary antibodies (about 100 µl) diluted in the saturation solution are then added for 30 minutes to 2 h, at room temperature or at 37° C. The excess is eliminated after several washes. If necessary, a substrate (100 µl) is added for 1 to 5 minutes in the dark at room temperature, followed by a stop solution.

The results of the titrations allow the two values obtained for the two distinct forms to be compared for the same mammal. Such comparisons carried out simultaneously in one or more mammals presenting a latent form of tuberculosis and in one or more mammals presenting an active form of tuberculosis produce very different results because of the specific behaviour of the immune response which occurs in infected mammals.

It has previously been shown in a French patent (FR-A-01/14953) that the native HBHA protein (nHBHA) is methylated on its lysine residues in the C terminal portion. In contrast, the recombinant HBHA protein (rHBHA) has a different degree of methylation since it does not possess such post-translational modifications.

The use of native and recombinant forms has thus shown that biological samples from mammals having an active form of tuberculosis contain a comparable quantity of antibodies directed against the active and recombinant forms thus showing that in those mammals, the same portion of the protein (the N terminal end) is recognized. In contrast, biological samples from mammals presenting a latent form of tuberculosis show a titer of antibodies directed against the native form which is higher than the titer of antibodies directed against the recombinant form, indicating that in those mammals there is preferential recognition of the methylated native form. These results thus allow the latent and active forms of tuberculosis to be distinguished by comparison of the titers of antibodies directed against the native and recombinant forms of HBHA.

Two other distinct forms of HBHA used in the context of the present invention are the rHBHAΔC fragment representing the N terminal portion of the protein (amino acids 1 to 160), and a methylated C terminal portion. A comparison of the titers of antibodies derived from the biological sample has revealed that in mammals presenting a latent form of tuberculosis, a predominance of antibodies recognizing the methylated C terminal fragment is observed, while in mammals with an active form of tuberculosis, a predominance of antibodies recognizing the rHBHAΔC fragment is observed.

Such a method comprising titration of antibodies may be carried out on any biological sample containing IgGs. In a further aspect of the invention, said method is carried out on blood samples.

The invention also provides a kit for detecting and differentiating between a mammal presenting a latent tuberculosis and a mammal presenting an active tuberculosis, said kit comprising:
  two distinct forms of HBHA, as defined above, on the one hand native HBHA and recombinant HBHA and on the other hand the rHBHAΔC fragment and the methylated C terminal fragment of HBHA;
  reagents for constituting a medium suitable for carrying out an immunological reaction between the antibodies contained in the biological sample from said mammal and the distinct forms of HBHA; said reagents encompass all compounds necessary for interactions between the antibody and the distinct forms of HBHA, as well as any compound which may increase, or improve said interactions or render them more specific;
  reagents allowing detection of immunological complexes formed during said immunological reaction. Said reagents comprise any compound which can reveal or detect the reaction between the antibody and the distinct forms of HBHA mentioned above. The reagents include secondary antibodies, optionally radioactively labeled or coupled with fluorochromes, as well as any molecule, which can intensify or modulate the detection signal.

The kit optionally comprises one or more reference tissue(s) or biological sample(s) which may be used as a negative control (sample deriving from an uninfected mammal; stage TB0) or as a positive control (stages TB2 and/or TB3).

The conventional methods, based on the HBHA-specific IFN-γ secretion, presently seem sufficient to identify TB latent patients in a healthy control population, as well as to discriminate between TB latent and TB active patients, as shown in the ROC curves of FIG. 12. However, these methods can be greatly improved by taking in account the ESAT-6 specific IFN-γ secretion. Therefore, the invention describes an alternative method to these conventional methods, that is based on both HBHA-specific and ESAT-6 specific IFN-γ secretions.

The invention concerns a second in vitro method for detecting and differentiating between a mammal presenting a latent tuberculosis and a mammal presenting an active tuberculosis or for identifying a mammal presenting a latent tuberculosis within a healthy population, said method comprising
  a) obtaining a biological sample from said mammal;
  b) bringing said biological sample into contact, in an independent manner, with the native form of HBHA and with ESAT-6 under conditions which allow the secretion of IFN-γ;
  c) measuring the HBHA-specific IFN-γ secretion and the ESAT-6-specific IFN-γ secretion; and
  d) calculating the ratio between the HBHA-specific IFN-γ secretion and the ESAT-6 specific IFN-γ secretion,
  in which said ratio obtained in a mammal presenting a latent tuberculosis is higher than the ratio obtained in a mammal presenting an active tuberculosis or obtained in a mammal not infected by *M. tuberculosis*.

In step a), the biological sample is obtained either from a healthy population, i.e., from individuals who do not present tuberculosis symptoms, or from a population infected by *M. tuberculosis*. The aim of the method within a healthy population is to identify individuals infected by *M. tuberculosis* but not presenting symptoms (latent TB) among individuals having no tuberculosis symptoms. In contrast, the aim of the method within a population of infected patients is to discriminate between patients having an active form of tuberculosis and patients having a latent form of tuberculosis.

This method comprises bringing a biological sample into contact with the native form of HBHA and independently into contact with ESAT-6 (early secreted antigen target 6). The expression "in an independent manner" means that the sample is brought into contact with HBHA and, separately in space, into contact with ESAT-6. Adding these two molecules to the biological sample will stimulate the cells present in said sample and cause the secretion of cytokines such as IFN-γ.

Bringing the sample into contact with HBHA and ESAT-6 is carried out under conditions which will allow the secretion of IFN-γ. Hence, the choice of medium, the pH and the temperature of the medium for contact, the contact period, the dilution of the biological sample, the concentrations of HBHA proteins may be modified by the skilled person as a function of the nature of the sample.

IFN-γ secretion is measured using any technique known to the skilled person, such as ELISA, ELISPOT, flow cytometry (PACS), quantitative RT-PCR following contact of the sample with HBHA, respectively termed HBHA-specific IFN-γ, and that following contact of the sample with ESAT-6, termed HBHA-specific ESAT-6. Modifications may be made by the skilled person concerning the parameters which can allow detection of IFN-γ secretion, such as the antibodies, their labeling and the interaction conditions. The ELISA conditions are the same as those described above, the buffered solution containing an anti-IFN-γ antibody instead of proteins distinct from HBHA. A secondary antibody directed against IFN-γ is also used.

Calculating the ratio between the HBHA-specific IFN-γ and the ESAT-6 specific IFN-γ allows the latent form to be distinguished from the active form of tuberculosis. Hence, in mammals with the latent form, a very high ratio is obtained, of more than 1, more than 50, more than 100, more than 200 or more than 300. Thus, a ratio in the range 100 to 400 confirms the latent form of tuberculosis. In contrast, in mammals with the active form or in mammals not infected by *M. tuberculosis*, this ratio is very low and less than 1, less than 0.75 or less than 0.5. Hence, a ratio of zero or less than 0.5 confirms either a patient with an active TB form in a group of patients infected by *M. tuberculosis* (for example having a positive tuberculin test) or a patient not infected by *M. tuberculosis* within a healthy population (tuberculosis symptom-free).

This second method is carried out on any biological sample routinely used in tuberculosis diagnosis such as bronchial aspirations, broncho-alveolar lavages (BAL), gastric lavages, sputum, samples of effusion fluids such as pleural, abdominal and articular fluids, cerebrospinal fluids, cephalorachidian fluids, synovial fluids, peritoneal fluids, pericardiac fluids and other body fluids, lymph node biopsies, transbronchial biopsies, pleural and hepatic biopsies, medullary and lumbar punctures, urine or blood samples, and pus aspirations. In one implementation of the invention, this method will be carried out with lymphocytes extracted by any method known to the skilled person from blood sampling. In a further implementation, the PBMCs are extracted from peripheral blood.

In a further implementation, after obtaining the biological sample and before bringing said sample into contact, the method described above comprises a supplemental step of culturing the biological sample. Culture will be adapted to the nature of the biological sample.

The present invention also concerns a kit for detecting and differentiating between a mammal presenting a latent tuberculosis and a mammal presenting an active tuberculosis or for identifying a mammal presenting a latent tuberculosis within a healthy population, said kit comprising:
  the native form of HBHA and ESAT-6;
  reagents for constituting a medium for carrying out contact in an independent manner, cells present in the biological sample from said mammal with native HBHA and ESAT-6; the reagents include those described above for the preceding kit;
  reagents for detecting the IFN-γ secretion following contact. The secreted IFN-γ will be measured using any known technique and primary antibodies specific for IFN-γ, optionally labeled, or secondary antibodies, optionally labeled, capable of recognizing the primary antibody may be included in the kit, as well as any molecule which can amplify or modulate the detection signal.

Optionally, the kit may also comprise one or more reference biological tissues or sample(s) which may be used as a negative control (sample deriving from an uninfected mammal; stage TB0) or as a positive control (stages TB2 and/or TB3).

In a further implementation, the kit comprises a culture medium and any compound participating in culturing the sample thereof, prior to contact with native HBHA or ESAT-6.

The present invention also pertains to a third in vitro method for detecting and differentiating between a mammal presenting an active tuberculosis and a mammal not infected by *M. tuberculosis* or presenting a latent tuberculosis, said method comprising
  a) obtaining a biological sample from local infection sites in said mammal;
  b) bringing said biological sample into contact with the native or recombinant form of HBHA under appropriate conditions to obtain an effect on IFN-γ;
  c) measuring the effect of contact on the HBHA-specific IFN-γ
  in which the effect on HBHA-specific IFN-γ is greater in a mammal presenting an active tuberculosis than in a mammal not infected by *M. tuberculosis* or presenting a latent tuberculosis.

Within the context of the invention, the expression "local infection sites" encompasses any site in which the pathogen *Mycobacterium tuberculosis* is established and wherein an infection has been caused. This definition thus includes the lungs, the lymph node, the pleura (pleural space), the joints, the bones, the genitor-urinary tract, the meninges, the peritoneum, the gastrointestinal tract, the central nervous system, the adrenal glands or the pericardium. In this method, all samples of blood origin including PBMCs are excluded.

This method comprises bringing a biological sample into contact with the native or recombinant form of HBHA causing the stimulation of cells of said sample. The expression "recombinant form of HBHA" as used in this third method means the entire non methylated form of HBHA such as that purified from the *E. coli* strain (BL21(DE3) (pET-HBHA).

The effect of said stimulation on IFN-γ is then determined. The term "effect on IFN-γ" means any modification regarding IFN-γ expression, both on the transcriptional (mRNA) or translational (protein) level, regarding IFN-γ degradation, maturation (such as glycosylation) or secretion.

A sample derived from local infection sites is brought into contact with HBHA under conditions that are appropriate for obtaining an effect on IFN-γ, which may be modified by the skilled person, such as in the choice of medium, the pH and the temperature of the medium for contact, the contact period, the dilution of the biological sample, and the concentrations of HBHA protein.

In one implementation of the invention, the quantity of secreted IFN-γ is measured using any known technique for measuring the quantity of a compound, such as ELISA, ELISPOT, flow cytometry (FACS) or quantitative RT-PCR.

The quantity of HBHA-specific IFN-γ secreted from a biological sample from a mammal presenting an active tuberculosis is more than 1000, more than 2000 pg/ml, more than 5000 pg/ml or more than 10000 pg/ml. Hence, a quantity in the range 5000 to 45000 pg/ml or in the range 10000 to 45000 pg/ml confirms an active form of tuberculosis. In contrast, a quantity of HBHA-specific IFN-γ, secreted from a biological sample, of zero or less than 100, 400 or 1000 pg/ml confirms the absence of *M. tuberculosis* infection or a latent form of tuberculosis.

In a further implementation, the proportion of cells positive for IFN-γ labeling is quantified by the difference between the percentage of cells expressing IFN-γ after stimulation with HBHA for 16 hours and the percentage of cells producing IFN-γ without stimulation (spontaneous secretion). This calculation is carried out on cells of the biological sample targeted for the quantification protocol, such as lymphocytes, CD4$^+$ cells, or any other lymphocyte sub-population. Labeling is carried out by any means known. for intracellular labeling of a compound and which may use permeabilization agents such as saponin (0.01% to 0.1%), triton (0.1%), digitonin and/or cell fixing agents such as 2% paraformaldehyde, or antibodies, optionally radioactively labeled or coupled to fluorochromes.

After contact of the sample with HBHA, Brefeldin A is added (10 μg/ml) to the sample for 3 to 5 hours at 37° C. or room temperature to block any secretion of cells contained in the sample. The cells are then fixed with a fixing agent such as those described above for 15 to 30 minutes at 4° C. then permeabilized with permeabilization agents such as those described above, for 15 to 30 minutes at room temperature, in the dark. The primary and secondary antibodies are diluted in a permeabilization solution (10 mg/ml) and added for incubation at 15 to 30 minutes at 4° C. The surface antigens such as CD4 or CD8 are labeled either before fixing with the fixing agent to which they are sensitive, or after permeabilization for those which are resistant to fixing. The labeled cells are then analyzed by flow cytometry.

Hence, the proportion of cells obtained from the biological sample from a mammal presenting an active tuberculosis is more than 0.3%, more than 0.5%, more than 0.75% or more than 1%. Values of 5%, 10% and up to 15% may be obtained. In contrast, the proportion of cells obtained from a biological sample from a mammal not infected by *M. tuberculosis* or presenting a latent tuberculosis is zero or less than 0.2% to 0.3%.

This method can demonstrate the active form of tuberculosis in a mammal. In contrast, a low secretion of IFN-γ or a small quantity of intracytoplasmic IFN-γ in the values cited above reveals an absence of the active form of tuberculosis, and may be interpreted as an absence of infection by *Mycobacterium tuberculosis* or as a latent form of tuberculosis.

Optionally, a step is added in this method between obtaining the biological sample and bringing it into contact with the sample, consisting of culturing said biological sample.

In one implementation, the biological sample is selected from the group constituted by bronchial aspirations, bronchoalveolar lavages (BAL), gastric lavage, sputum, samples of effusion fluids such as pleural, abdominal and articular fluids, cerebrospinal fluids, cephalorachidian fluids, synovial fluids, peritoneal fluids, pericardiac fluids, lymph node biopsies, transbronchial biopsies, pleural and hepatic biopsies, medullary punctures and lumbar punctures, urine samples and pus aspirations.

In a further implementation of the invention, the cells used for said method are T lymphocytes such as CD3$^+$CD4$^+$ T lymphocytes.

The invention also concerns a kit for detecting and differentiating between a mammal having an active tuberculosis and a mammal not infected by *M. tuberculosis* or presenting a latent tuberculosis, said kit comprising:

the native or recombinant form of HBHA;

reagents for constituting a medium suitable for bringing cells present in the biological sample from said mammal into contact with native or recombinant HBHA; the reagents include those described above in the preceding kits;

reagents allowing the detection of IFN-γ following contact. The secreted or intracytoplasmic IFN-γ is measured using any known technique, and primary antibodies specific for IFN-γ, which may be labeled, secondary antibodies, which may be labeled, capable of recognizing the primary antibody, and any molecule which may amplify or modulate the detection signal, may be provided in the kit.

The kit optionally comprises. one or more reference tissues or biological samples which may be used as control: a sample deriving from an uninfected mammal (stage TB0), a sample from stage TB2 and/or a sample from stage TB3.

In one implementation, the kit comprises a culture medium and any compound participating in culturing the sample prior to contact with HBHA.

The following examples are given to illustrate the present invention and in no way limits the scope of the invention.

EXAMPLES

Example 1

Origin of Blood Samples

Blood samples were obtained from tuberculous patients and from patients with latent tuberculous after having obtained their consent. The tuberculous patients were selected on the basis of a positive direct examination and/or a positive culture for *Mycobacterium tuberculosis*. All subjects were enrolled before the end of the first three weeks of treatment. The subjects having a latent form of tuberculosis were selected on the basis of a positive delayed hypersensitivity test to tuberculin (diameter of induration over 18 mm at the time of diagnosis). An active form of tuberculosis was excluded on the basis of a normal thorax radiograph. All of the patients were seronegative for HIV and none had received immunosuppressor treatment. All of the subjects were living in Europe at the time of recruitment

Example 2

Other Samples

Broncho-alveolar lavage fluid (BAL) was removed, by fibroscopy, after injecting about 200 ml of physiological water. The volume removed was then centrifuged (about 10 ml).

Pleural, articular, peritoneal, cephalorachidian and other fluids were collected in sterile syringes and were centrifuged as soon as they arrived at the laboratory.

For ganglia or other suspect masses, surgical exeresis was carried out. Upon its arrival at the laboratory, the anatomical fragment collected was morcellated and incubated in a culture medium to allow progressive release of cells from the tissue.

Example 3

Antigens

The native form of HBHA (nHBHA) was purified from *M. bovis* BCG by heparin-sepharose chromatography followed by high pressure fluid chromatography (HPLC) as described elsewhere (14). An HPLC chromatogram and SDS-PAGE analysis after staining with Coomassie Blue proved that the preparation had no protein contamination. No traces of glycolipids were found using gas chromatography. The limulus test showed that the lipopolysaccharide concentration was less than 10 pg/ml.

The non methylated recombinant form (rHBHA) was purified from the *E. coli* strain (BL21(DE3)(pET-HBHA). The degree of methylation of the recombinant protein compared with that of the native protein was described in French patent FR-A-01/14953.

The truncated recombinant form of the C terminal portion (rHBHAΔC) was purified from the *E. coli* strain (BL21(DE3) (pET-rHBHAΔC). This truncated form rHBHAΔC was described in Pethe et al (2000 Journal of Biological Chemistry 275(19): 14273-14280, incorporated into the present description by reference) and is derived from recombinant HBHA protein from which amino acids 161 to 199 had been deleted.

The isolated C terminal peptide, synthesized by combination with pre-methylated amino acids, corresponds to amino acids 161 to 199 of the HBHA protein, and has the following sequence:
KKAAPAKKAAPAKKAAPAKKAAAKKAPA-
KKAAAKKVTQK (SEQ ID NO: 1) (12, 13). Pethe et al (Proc Natl Acad Sci 2002; 99: 10759-10764) and Temmerman et al (Nat. Med. 2004 Sep. 10(9): 935-941) are hereby incorporated by reference.

Example 4

Detection of Specific IgG of HBHA

ELISA was used to detect anti-nHBHA, -rHBHA, -rHBHAΔC and -C peptide (isolated C-terminal peptide) IgG. In detail, 96-well polystyrene plates (Maxisorp Nunc) were incubated overnight at 4° C. with 50 µl/well of a solution of 1.5 µg/l of antigen diluted in PBS (nHBHA, rHBHA, rHBHAΔC or C-peptide). The plates were washed three times with PBS-Tween 20 (0.05%) and saturated with a 1% casein solution in PBS for 1 h at 37° C. After washing, the sera from patients, diluted in a PBS-Tween 20 solution (0.05%) (dilutions of 1:50 to 1:12800) were disposed for 30 min in the wells at the room temperature and with stirring. Goat anti-human IgG antibodies coupled with biotin diluted 250 times in PBS-Tween 20 (0.05%) were the secondary antibodies used (biotinylated goat anti-human IgG—Southern Biotechnologies Associates, Birmingham, USA 2040-08), their presence was revealed by 50 µl/well of a peroxidase solution (extravidin peroxidase—conjugated E2886—Sigma) diluted by 1:1000 (0.5% casein). 50 µl of a substrate solution (0.1 mg/ml of 3,3',5,5'-tetramethylbenzidine and 1 µl/ml of 30% hydrogen peroxide in 0.1 M sodium citrate, pH 5) was added after washing for a period of 10 to 30 minutes in darkness. The reaction was stopped by 25 µl/well of hydrochloric acid (2 mMol/L). The antibody titer is expressed as the last serum dilution which is considered to be positive with respect to a pool of negative sera.

Example 5

Secretion of Gamma Interferon by PBMCs in Response to nHBHA/ESAT-6 (ELISA)

PBMCs were obtained by density gradient centrifuging of peripheral blood samples (lymphoprep—Nycomed Pharma). Said PBMCs were resuspended in a concentration of $2 \times 10^6$ cells/ml in culture medium (complete RPMI: RPMI 1640 (BioWhittaker) supplemented with 40 µg/ml of gentamycin, 50 µM of 2-mercaptoethanol, 1X non essential amino acids (Life Technologies) and 10% of foetal calf serum (FCS)). The cells were stimulated with 2 µg/ml of nHBHA and in parallel with 5 µg/ml of early secreted antigen target 6 (ESAT-6) (Statens Serum Institut, Denmark) for a period of 96 hours in an atmosphere of 5% $CO_2$ at 37° C. In some experiments, blocking antibodies were added in a concentration of 5 µg/ml: anti-TGF-β 1,2,3 (mouse IgG1, R&D System) and the results were compared with those obtained in the presence of control antibodies (mouse IgG1; R&D System). The supernatants were collected after 4 days of culture to measure the secreted IFN-γ using ELISA (IFN-γ Cytoset, Biosource).

Example 6

Local Gamma Interferon Response

Example 6a

Biological Fluids and Anatomical Parts

The analyzed biological fluids were pleural, articular and peritoneal fluids. The anatomical parts analyzed were biopsies excised from ganglia or from various suspect masses. Isolation of nucleated elements from the biological fluids was carried out by a first filtration (cellular sieve, Nylon 100 µm Falcon® 352360) followed by centrifuging at 2300 rpm for 15 minutes. The red globules present in the cell residue were lysed if necessary. The cells were then resuspended in a complete RPMI solution. Nucleated elements from the anatomical samples were isolated by morcellation of the parts and incubation overnight in a complete RPMI solution at 37° C. and in a 5% $CO_2$ atmosphere. The supernatants were recovered and the parts were rinsed to recover any cells which were still accessible. These harvested fluids were then centrifuged at 2300 rpm for 15 minutes. The red globules were lysed if necessary. The cell residue was resuspended in a complete RPMI solution.

Example 6b

Antigenic Stimulation

When the number of isolated cells was sufficient (pleural fluids), they were stimulated in vitro in the same manner as the PBMCs and the concentrations of secreted FN-γ were measured in the culture supernatants after 96 hours stimulation in vitro by HBHA. As for the PBMCs, analysis of IFN-γ synthesis by these cells could also be carried out by flow cytometry after brief in vitro stimulation by HBHA as described below for broncho-alveolar fluids, articular or peritoneal fluids, ganglia, etc. The isolated cells ($2\times10^6$/ml) were stimulated in vitro by HBHA at a concentration of 10 µg/ml for a period of 16 to 18 hours. The cytokine secretions from cells were then blocked by incubating for 4 hours in the presence of Brefeldin A (10 µg/ml—Brefeldin A—Sigma) and the presence of IFN-γ in the cells was analyzed by flow cytometry after labeling the cells. After fixing the cells, they were permeablized (Fix and Perm; Cell Permeabilization Kit—Caltag Laboratories), washed, then incubated in the dark for 30 min in the presence of antibodies coupled to fluorochromes (anti-CD3 PerCP, anti-CD4 APC, anti-IFN-γ PE, all obtained from Becton, Dickinson). The percentage of positive cells was then analyzed with a FACSCalibur cytometer, initially targeting lymphocytes on the basis of their size and granularity, and then the different lymphocyte sub-populations as a function of surface marker expression.

Example 7

Statistical Analyses

For unpaired data, the Mann-Whitney non parametric U test or the non parametric Kruskall-Wallis test was carried out followed by post-test comparisons using Dunn tests. Paired data were analyzed by the Wilcoxon or Friedman test.

Receiver operating characteristic (ROC) analysis: each point on the curve (FIG. 12) corresponds to a specific pair of sensitivity and specificity, calculated according to values given in tables 1, 2 or 3. The complete curve (and particularly the area beneath it) gives an overview of the overall test. Good curves lie closer to the top left corner, while in the worst case a diagonal line (dashed line) is obtained.

The total area under the ROC curve is a measure of the performance of the diagnostic test since it reflects the test performance at all possible cut-off levels. The area lies in the interval [0.5-1] and the larger area, the better performance of the test. The accuracy of the test is classified according to the area under the curve, as follows: [0.9-1]: excellent; [0.8-0.9]: good; [0.7-0.8]: fair; [0.6-0.7]: poor and [0.5-0.6]: fail.

The following definition are used:
Sensitivity: probability of having a positive test among the patients having a positive diagnostic: true positive (TP);
Specificity: probability of having a negative test among the patients who have a negative diagnostic: true negative (TN);
(1-specificity): probability of having a positive test among the patients having a negative diagnostic: false positive (FP);
(1-sensitivity): probability of having a negative test among the patients who have a positive diagnostic: false negative (FN);

The ROC test enables to find an optimal cut-off value, for which the sensitivity and specificity are high.

Results

Figure 1:
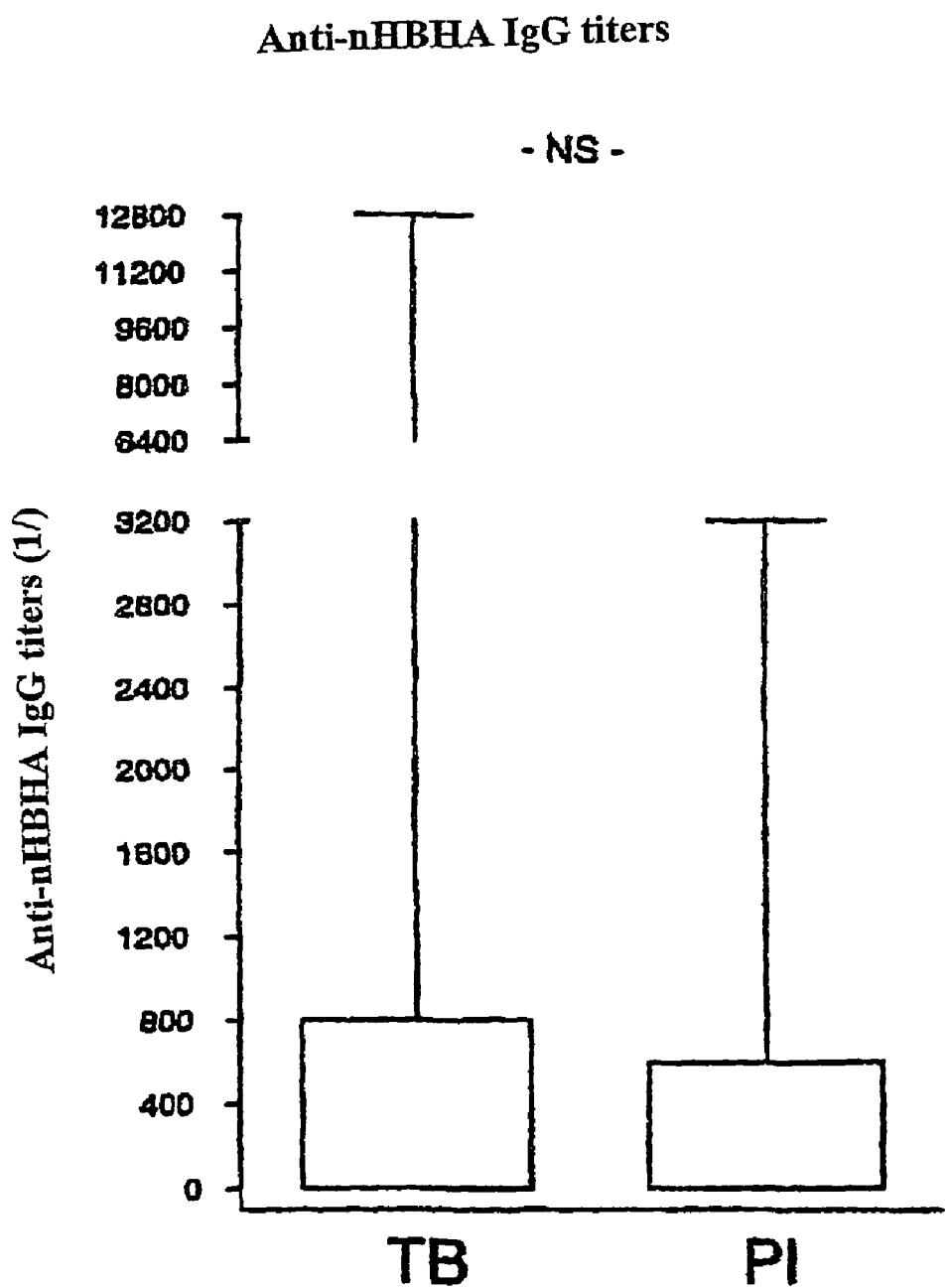
FIG. 1 concerns titers of HBHA-specific IgG in tuberculous patients (TB) and in subjects presenting a latent tuberculosis (PI). The rectangles show the 25$^{th}$ and 75$^{th}$ percentiles. The vertical lines show the maximum values.

1. Humoral Response nHBHA-specific IgGs were detected in the serum from about 40% of subjects infected with *Mycobacterium tuberculosis*, whether they were in good health (primo-infected subjects or latent form) or they were diseased and presented with tuberculosis (active form). The antibody titers found in these two groups of subjects were not different (FIG. 1).

Figure 2B:
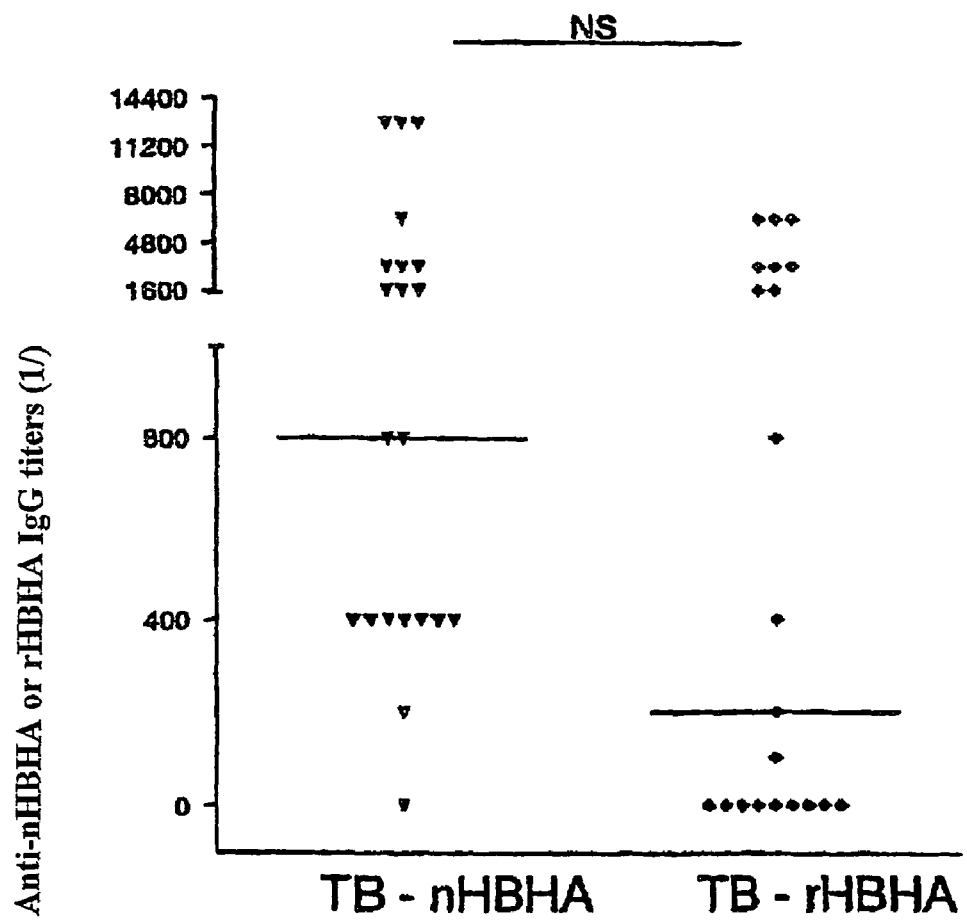
Figure 3B:
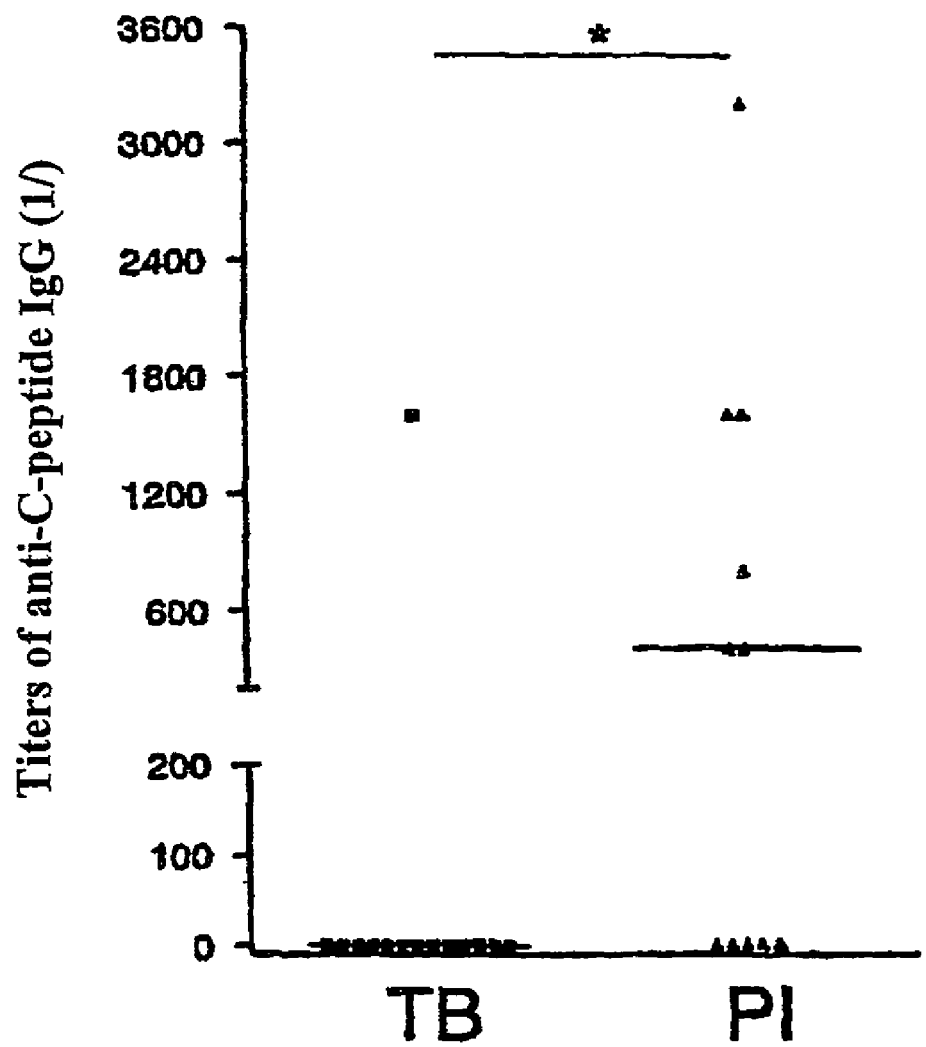

However, a comparison of titers of antibody directed against the native methylated form of HBHA (nHBHA) with those directed against the non methylated recombinant form (rHBHA) sparked the hypothesis that the antibodies were different depending on whether the patients infected with *Mycobacterium tuberculosis* were diseased (active form) or not (latent form). As can be seen in FIG. 2, the titers of anti-nHBHA IgG were significantly higher than the anti-rHBHA IgG titers (p=0.0015) in primo-infected subjects (FIG. 2A) while the differences were not significant in tuberculous patients (FIG. 2B). We then assayed IgG directed, on the one hand, against a truncated recombinant form of HBHA composed solely of the N-terminal domain of the molecule (rHBHAΔC) and on the other hand those directed against the methylated C-terminal peptide. These results, shown in FIG. 3, indicate that the anti-HBHA IgG present in the serum from tuberculous patients recognize rHBHAΔC (FIG. 3A) while the antibodies from primo-infected subjects recognize the methylated C-terminal peptide (FIG. 3B). Depending on the type of antibody present in the serum from subjects infected with *Mycobacterium tuberculosis*, those could thus be classified into two groups, primo-infected or diseased, depending on whether the IgG were directed against the non methylated N-terminal portion of HBHA or against the methylated C-terminal portion.

2. Secretion of IFN-γ by Circulating Lymphocytes a. We have previously shown that the secretion of IFN-γ in response to the native form of HBHA by PBMCs is significantly greater in primo-infected subjects than in tuberculous patients. The discrimination obtained was not, however, sufficient to be used for diagnostic purposes. An increase in the number of subjects tested allowed a selection to be made among primo-infected subjects, of those for whom the presumed date of infection was less than five years. The results shown in FIG. 4 show that discrimination between the two groups is slightly better but still insufficient.

b. In order to evaluate better the potential value of the IFN-γ secretion induced by native HBHA to diagnose a latent infection by *Mycobacterium tuberculosis*, ROC (receiver operating curves) were produced to establish the concentration of IFN-γ (optimal cut-off) which gives the best sensitivity/specificity couple for the question that was posed.

1) Diagnosis of Latent TB Patients Within a Healthy Population (Distinction Between Latent TB Patients and not Infected Persons)

Since persons presenting a latent TB (IP) are not diseased but represent a potential source of dissemination of Koch's bacillus, the test must be able to identify such persons within a healthy population. Therefore, ROC curves were produced on the basis of the concentrations of IFN-γ induced by HBHA and secreted by PBMCs from control subjects (not infected by *M. tuberculosis*—n=14) and from persons presenting a latent TB (n=46) defined on the basis of the results of an intradermal reaction to tuberculin positive PPD, which is the reference diagnostic criterion (Table 1).

TABLE 1 nHBHA-specific IFNγ value in latent TB patients and control (healthy) individuals.

| Status | Number | nHBHA-specific IFNγ value (pg/ml) |
|---|---|---|
| Latent TB | 46 | 3390, 35, 2500, 18210, 519, 72, 7576, 997, 223, 12750, 32700, 4025, 373, 20505, 1727, 28400, 15820, 16580, 395, 13528, 3790, 6496, 2500, 21440, 3035, 2040, 1545, 16000, 1, 3305, 35550, 121000, 32600, 5092, 988, 269, 608, 78, 1256, 1455, 14, 131, 4933, 532.9, 3565.7, 249.45 |
| Control | 14 | 4, 0, 62, 87, 3, 2, 21, 16, 0, 90, 0, 83, 36, 31.6 |

In such experiment, "positive" and "negative" persons are defined as follows:

TP: probability of having a positive test (over the optimal cut-off) among the patients having a positive intradermal reaction to tuberculin;

FP: probability of having a negative test (under the optimal cut-off) among the patients who have a negative intradermal reaction to tuberculin;

FN: probability of having a positive test (over the optimal cut-off) among the patients having a negative intradermal reaction to tuberculin;

TN: probability of having a negative test (under the optimal cut-off) among the patients who have a positive intradermal reaction to tuberculin;

The ROC curve shown in FIG. 12A below is excellent, since the area under the curve is 0.95 (95% confidence interval: 0.90-1.00; P<0.0001). For a concentration of IFN-γ of more than 110 pg/ml (optimal cut-off), the sensitivity of the test for a diagnosis of latent TB is 89.13% (CI95: 76.43-96.38) with a specificity of 100% (CI95: 76.84-100).

It is noteworthy that controls in this ROC test are persons that were not vaccinated for tuberculosis (BCG). The possible interference of the BCG vaccination were previously tested and reported in 2002 (Masungi et al. J. Inf. Dis. 2002; 185 : 513-20). These preliminary experiments showed that the circulating lymphocytes from 15 BCG-vaccinated persons (BCG-vaccinated more than 10 years before the blood sampling) do not secrete IFN-γ in response to HBHA, whereas they do in response to PPD.

However, since the study concerns TB discrimination in a healthy adult population and that in most countries vaccination is performed in childhood, it appeared appropriate to test persons vaccinated more than 10 years. From these persons, 5 give a positive intradermal reaction to tuberculin, and 3 give doubtful results. Moreover, circulating lymphocytes from 10 of these healthy BCG-vaccinated persons secrete IFN-γ in response to PPD.

In conclusion, it appears that the BCG-vaccination do not disturb the possible diagnostic interest to discriminate latent TB patients among an healthy population, based on in vitro IFN-γ induction by HBHA.

2) Diagnostic Differential Between Latent TB and Active TB Patients

When a patient presents a clinical history compatible with tuberculosis and his or her intradermal reaction to tuberculin is positive, it is important to differentiate tuberculosis from another disorder which may occur in a patient who also has latent TB. Thus, the test must identify latent TB patients in a population of patients infected by *M. tuberculosis*. Thus, ROC curves were produced on the basis of the concentrations of IFN-γ induced by HBHA and secreted by PBMCs on the one hand from subjects presenting a latent TB defined on the basis of the results of an intradermal reaction to tuberculin, which is the critical diagnostic reference (n=46), and on the other hand from patients presenting untreated active TB (n=50) (Table 2).

TABLE 2 nHBHA-specific IFNγ value in latent TB and active TB patients

| Status | Number | nHBHA-specific IFNγ value (pg/ml) |
|---|---|---|
| Latent TB | 46 | 3390, 35, 2500, 18210, 519, 72, 7576, 997, 223, 12750, 32700, 4025, 373, 20505, 1727, 28400, 15820, 16580, 395, 13528, 3790, 6496, 2500, 21440, 3035, 2040, 1545, 16000, 1, 3305, 35550, 121000, 32600, 5092, 988, 269, 608, 78, 1256, 1455, 14, 131, 4933, 532.9, 3565.7, 249.45 |
| Active TB | 50 | 14, 12, 41, 82, 167, 18, 11, 50, 50, 25, 398, 15, 33, 19, 1, 45, 2, 1, 671, 42, 5, 27, 317, 1, 1, 15, 60, 13, 426, 2249.6, 1145.8, 124.79, 4177.6, 96.7, 586.78, 3317.5, 23, 17748, 781.42, 17, 76, 138, 20, 43, 46, 201, 441, 322, 676, 340.68 |

In such experiment, positive and negative persons are defined as follows:

TP: probability of having a positive test (over the optimal cut-off) among the patients having tuberculosis syndromes;

FP: probability of having a negative test (under the optimal cut-off) among the patients who don't have tuberculosis syndromes;

FN: probability of having a positive test (over the optimal cut-off) among the patients not having tuberculosis syndromes;

TN: probability of having a negative test (under the optimal cut-off) among the patients who have tuberculosis syndromes;

The ROC curve obtained (FIG. 12B) is good, since it produces an area under the curve of 0.855 (IC95: 0.777-0.932). For a threshold IFN-γ concentration of 480 pg/ml (optimal cut-off), the sensitivity to the test for a diagnosis of latent TB is 76.09% (CI95: 61.23-87.41) with a specificity of 82% (CI95: 68.56-91.42).

It should be noted that the results for the ROC curve are substantially poorer when considering the concentrations of PPD-induced IFN-γ in PBMCs. This curve (FIG. 12C), calculated on the basis of results obtained for 31 latent TB and 47 active TB (Table 3), has an area under the curve of only 0.73 (CI95: 0.62-0.84).

TABLE 3

PPD-specific IFNγ value in latent TB and active TB patients

| Status | Number | PPD-specific IFNγ value (pg/ml) |
|---|---|---|
| Latent TB | 31 | 4485, 1057, 25200, 44300, 3760, 2920, 16750, 3520, 61300, 14805, 20700, 4606, 25500, 26240, 27000, 23525, 16950, 26000, 8780, 23650, 285000, 126000, 6400, 12332, 42932, 24137, 822, 2763, 7174, 7746.8, 9435.4 |
| Active TB | 47 | 23, 4650, 445, 4660, 1541, 729, 1448, 1707, 3800, 46800, 3592, 13, 1004, 430, 100, 1135, 20625, 50, 776, 7714, 877, 525, 7742, 1004, 86, 5408, 7748, 45, 4392, 1882, 46, 2211, 4, 15882, 8, 37738, 630, 34440, 20817, 34680, 7820, 23358, 838, 4014, 23908, 24783, 8852, 8516, 17145, 10781 |

In view of the above results, it therefore appears that the secretion of IFN-γ induced by HBHA allows latent TB patients to be differentiated from individuals not infected by *M. tuberculosis* and from active TB patients, which is not possible with the other conventional tests, either on the basis of the intradermal reaction to tuberculin test or on the basis of the secretion of IFN-γ induced by PPD or by ESAT-6. This seems mainly due to the better clinical selection of patients.

c. The literature reports that tuberculous patients secrete IFN-γ in response to ESAT-6, in contrast to primo-infected subjects, but discrimination is not good enough, as shown in FIG. 5.

d. We shall show that a calculation of the ratio between the secretion of nHBHA-specific IFN-γ and that induced by ESAT-6 can offer an excellent means for discriminating between primo-infected subjects who are not diseased and tuberculous patients (p=0.0003; n=8) (FIG. 6). Indeed, the ratio is about 0.1 pg/ml for active TB patients whereas the same ratio is about 146.2 pg/ml for latent TB patients, with no overlapping values.

These conclusions also apply for the identification of TB latent patient in a healthy population, since patients not infected by *M. tuberculosis* do not secrete IFN-γ, in response to ESAT-6 or in very low concentrations (data not shown).

Adding an antibody blocking anti-TGF-β can in many cases demonstrate that the absence of peripheral IFN-γ secretion in response to lymphocyte stimulation by HBHA clearly results from infection by *Mycobacterium tuberculosis* in the diseased patient and is not due to an absence of infection. As shown in FIG. 7, in the presence of an anti-TGF-β, IFN-γ secretions from PBMCs from tuberculous patients increase significantly (p=0.01). This is not observed with primo-infected patients.

3. Local Secretion of IFN-γ in Response to nHBHA

In tuberculous patients, in contrast to the absence of IFN-γ secretion by PBMCs in response to nHBHA, stimulation of cells derived from local infection sites such as pleural, alveolar, peritoneal and articular fluids allows a major IFN-γ response to be observed in response to stimulation by nHBHA or rHBHA, in contrast to control subjects not infected by *Mycobacterium tuberculosis* but presenting clinical and radiological signs which are comparable with those of tuberculosis. When the volume of the local sample allows isolation of a sufficient number of lymphocytes, these cells were stimulated by native HBHA and the quantity of IFN-γ present in the culture supernatants was measured by ELISA.

The results shown in FIG. 8 show that the concentrations of IFN-γ secreted by pleural cells after stimulation by HBHA are much higher than those secreted by cells from control, primo-infected or other subjects.

Discrimination between tuberculous patients and controls is much poorer if another antigen such as PPD is used to stimulate the pleural cells in vitro (FIG. 8).

The synthesis of HBHA-induced IFN-γ by the pleural cells of patients with a pleural effusion of tuberculous origin may also be demonstrated by analyzing lymphocytes using flow cytometry. This technique allows the measurement of the percentages of lymphocytes containing intracellular IFN-γ, and for which synthesis have been induced by brief in vitro stimulation by HBHA. This technique has the advantage of being extremely rapid, the HBHA stimulation period being overnight, all the more so as a result can be provided in 24 hours. The results shown in FIGS. 9 and 10 show that a large proportion of CD4+ lymphocytes from pleural fluid contain IFN-γ after HBHA stimulation, while this is not the case for pleural cells from effusions which are not of tuberculous origin, i.e., individuals not infected with *Mycobacterium tuberculosis* (FIG. 10). A study of the secretion of HBHA induced IFN-γ may be simplified by limiting the analysis to the lymphocyte window selected on the basis of their size and granularity.

In the case of pulmonary tuberculosis (with no pleural attack), a diagnosis may be made by studying lymphocytes from a broncho-alveolar lavage fluid. Indeed, after a brief in vitro stimulation with HBHA (overnight), a high proportion of local CD4+ lymphocytes (from local infection sites) contain intracellular IFN-γ, in contrast to lymphocytes from control patients (FIG. 11). Discrimination between tuberculous or non-tuberculous patients is better when local CD4+ cells are targeted rather than local CD8+ cells (FIG. 11), and the analysis can also be limited to the lymphocyte window.

During articular tuberculosis, a high percentage of lymphocytes isolated from the effusion (positive KB culture on fluid) synthesize IFN-γ after a brief in vitro HBHA stimulation, in contrast to local lymphocytes removed from control individuals having an effusion of non tuberculous origin (Table 4).

Finally, in the case of peritonitis of tuberculous origin, 31% of the lymphocytes present in this fluid contain intracellular IFN-γ after a brief in vitro HBHA stimulation. In one case of adenopathy of tuberculous origin, 1.8% of lymphocytes responded to HBHA by synthesizing IFN-γ, which allowed once more the diagnosis of the tuberculosis origin of the disorder, in less than 24 hours (Table 4).

TABLE 4

Percentage of CD4+CD3+ T lymphocytes containing IFN-γ, after stimulation by nHBHA of lymphocytes isolated on the tuberculous infection site, versus controls; -: no stimulation; Nd: not determined; KB+: positive to Koch *bacillus*.

| Sample type | Stimulation conditions | | |
|---|---|---|---|
| | — | PPD | nHBHA |
| Articular fluids (LA) | | | |
| LA KB+ | 3.90 | 16.00 | 8.96 |
| LA ctrl 1 | 0.10 | 0.20 | 0.20 |
| LA ctrl 2 | 0.22 | 0.63 | 0.11 |
| LA ctrl 3 | 0.05 | 0.09 | 0.09 |
| LA ctrl 4 | 0.05 | 1.03 | 0.10 |
| Peritoneal fluid KB+ | Nd | Nd | 31.360 |
| Tuberculosis adenopathy | 0.72 | 1.99 | 1.82 |

REFERENCES

1. Frieden T. R., Sterling T. R., Munsiff S. S. et. al. Lancet 2003; 362: 887-99.
2. Maher D., Chalet P., Spinaci S. et al. Treatment of tuberculosis: guidelines for national programmes. 2nd ed. Geneva: W.H.O. 1997.
3. Siddiqi K., Lambert M. L., Walley J. The Lancet Infect. Dis. 2003; 3: 288-296.
4. Strumpf I., Tsang A., Syre J. Am. Rev. Respir. Dis. 1979; 119: 599-602.
5. Travis W. et al. Mycobacterial pneumonias. In: West King D, ed. Non-Neoplastic Disorders of the Lower Respiratory Tract, 1st ed. Washington DC: AFIP; 2002: 579-87.
6. Hruban R H, Hutchins G M. Mycobacterial infections. In: Dail D H, Hammar S P, eds. Pulmonary pathology, 2nd ed. New York: Springler Verlag; 1994: 331-50.
7. Kaufmann S H.: Nat. Rev. Immunol. 201; 1: 20-30.
8. Converse P J, Jones S L, Astemborski J et al. J. Infect. Dis. 1997; 176: 144-50.

9. Andersen P., Munk M. E., Pollock J. M. et al. The Lancet 2000; 356: 1099-1104.
10. Pethe K., Ouech V., Daffe M. et al. Mol. Microbiol. 2001; 39: 89-99.
11. Pethe K., Alonso S., Biet F. et al. Nature 2001; 412: 190~194.
12. Pethe K., Bifani P., Drobecq H. et al. Proc. Natl Acad. Sci 2002; 99: 10759-10764.
13. Temmerman S., Pethe K., Parra M. et al. submitted.
14. Masungi C., Temmerman S., Van Vooren J. P. et al. J. Infect. Dis. 2002; 185: 513-520.

The invention claimed is:

1. An in vitro method for detecting and differentiating between a mammal presenting a latent tuberculosis and a mammal presenting an active tuberculosis, or for identifying a mammal presenting a latent tuberculosis within a healthy population, said method comprising:

a) obtaining a biological sample from said mammal;

b) bringing PBMC or lymphocytes present in said biological sample into contact, in an independent manner, with the native form of HBHA and with ESAT-6 under conditions allowing the secretion of IFN-γ;

c) measuring the HBHA-specific IFN-γ secretion and the ESAT-6-specific IFN-γ secretion; and d) calculating the ratio between the HBHA-specific IFN-γ secretion and the ESAT-6-specific IFN-γ secretion, in which said ratio obtained in a mammal presenting a latent tuberculosis is greater than the ratio obtained in a mammal presenting an active tuberculosis or obtained in a mammal not infected by *M. tuberculosis*.

2. The method according to claim 1, in which the ratio of secretions obtained from said PBMC or lymphocytes of the sample from a mammal presenting a latent tuberculosis or a mammal not infected by *M. tuberculosis* is greater than 1.

3. The method according to claim 1, in which the ratio of secretions obtained from said PBMC or lymphocytes of the sample from a mammal presenting a latent tuberculosis or a mammal not infected by *M. tuberculosis* is in the range 100 to 400.

4. The method according to claim 1, in which the ratio of secretions obtained from said PBMC or lymphocytes of the sample from a mammal presenting an active tuberculosis is less than 1.

5. The method according to claim 1, in which the ratio of secretions obtained from said PBMC or lymphocytes of the sample from a mammal presenting active tuberculosis is less than 0.5.

6. The method according to any one of claims 1 to 5, in which the biological sample is selected from the group constituted by bronchial aspirations, broncho-alveolar lavages (BAL), gastric lavage, sputum, samples of effusion fluids such as pleural, abdominal and articular fluids, cerebrospinal fluids, cephalorachidian fluids, synovial fluids, peritoneal fluids, pericardiac fluids and other body fluids, lymph node biopsies, transbronchial biopsies, pleural and hepatic biopsies, medullary punctures and lumbar punctures, urine or blood samples, and pus aspirations.

7. The method according to claim 1, in which said lymphocytes are T lymphocytes, CD4$^+$lymphocytes or CD3$^+$CD4$^+$T lymphocytes.

8. The method according to claim 1, comprising the supplemental step prior to step b) of culturing said PBMC or lymphocytes of the biological sample.

9. A kit for detecting and differentiating between a mammal presenting a latent tuberculosis and a mammal presenting an active tuberculosis or for identifying a mammal presenting a latent tuberculosis within a healthy population, said kit comprising:

the native form of HBHA and ESAT-6;

the reagents for constituting a medium for carrying out contact in an independent manner of PBMC or lymphocytes present in a biological sample from said mammal with native HBHA and ESAT-6; and reagents for detecting IFN-γ secretion following contact.

10. The kit according to claim 9, which further comprises a culture medium for the biological sample from said mammal to be detected.

11. An in vitro method for detecting and differentiating between a mammal presenting an active tuberculosis and a mammal not infected by *M. tuberculosis* or presenting a latent tuberculosis, said method comprising:

a) obtaining a biological sample from local infection sites from said mammal;

b) bringing lymphocytes from said biological sample into contact with the native or recombinant form of HBHA under conditions allowing an effect on IFN-γ to be obtained;

c) measuring the effect of said contact on the secretion of HBHA-specific IFN-γ;

in which the HBHA-specific IFN-γ effect is greater in a mammal presenting an active tuberculosis than in a mammal not infected by *M. tuberculosis* or presenting a latent tuberculosis.

12. The method according to claim 11, in which step c) consists of measuring the quantity of secreted IFN-γ following contact of said lymphocytes of the biological sample with the native or recombinant form of HBHA.

13. The method according to claim 12, in which the quantity of secreted HBHA-specific IFN-γ is greater in a mammal presenting an active tuberculosis compared with the quantity obtained in a mammal not infected by *M. tuberculosis* or presenting a latent tuberculosis.

14. The method according to claim 13, in which the quantity of HBHA-specific IFN-γ secreted from said lymphocytes of the biological sample from a mammal presenting an active tuberculosis is greater than 1000 pg/ml.

15. The method according to claim 13, in which the quantity of HBHA-specific IFN-γ secreted from said lymphocytes of the biological sample from a mammal presenting an active tuberculosis is greater than 5000 pg/ml.

16. The method according to claim 13, in which the quantity of HBHA-specific IFN-γ secreted from said lymphocytes of the biological sample from a mammal not infected by *M. tuberculosis* or presenting a latent tuberculosis is less than 1000 pg/ml.

17. The method according to claim 13, in which the quantity of HBHA-specific IFN-γ secreted from said lymphocytes of the biological sample from a mammal not infected by *M. tuberculosis* or presenting a latent tuberculosis is less than 100 pg/ml.

18. The method according to claim 11, in which step c) comprises calculating the proportion of lymphocytes, of said biological sample, containing intracytoplasmic IFN-γ after bringing said lymphocytes into contact with HBHA.

19. The method according to claim 18, in which said proportion of lymphocytes in a mammal presenting an active tuberculosis is greater than that obtained in a mammal not infected by *M. tuberculosis* or presenting a latent tuberculosis.

20. The method according to claim 18, in which said proportion of lymphocytes obtained from the biological sample from a mammal presenting an active tuberculosis is greater than 0.3%.

21. The method according to claim 18, in which said proportion of lymphocytes obtained from the biological sample from a mammal presenting an active tuberculosis is greater than 0.5%.

22. The method according to claim 18, in which said proportion of lymphocytes obtained from the biological sample from a mammal not infected by *M. tuberculosis* or presenting a latent tuberculosis is less than 0.3%.

23. The method according to any one of claims 11 to 22, comprising the supplemental step prior to step b) of culturing said lymphocytes of the biological sample.

24. The method according to claim 11, in which the biological sample is selected from the group constituted by bronchial aspirations, broncho-alveolar lavages (BAL), gastric lavage, sputum, samples of effusion fluids such as pleural, abdominal and articular fluids, cerebrospinal fluids, cephalorachidian fluids, synovial fluids, peritoneal fluids, pericardiac fluids, lymph node biopsies, transbronchial biopsies, pleural and hepatic biopsies, medullary punctures and lumbar punctures, urine samples, and pus aspirations.

25. The method according to claim 11, in which said lymphocytes are $CD3^+CD4^+T$ lymphocytes, T lymphocytes or $CD4^+$cells.

26. The kit for detecting and differentiating between a mammal presenting an active tuberculosis and a mammal not infected by *M. tuberculosis* or presenting a latent tuberculosis, said kit comprising:

the native or recombinant form of HBHA;

reagents to constitute a medium suitable for bringing lymphocytes present in a biological sample from said mammal into contact with HBHA;

reagents to detect IFN-γ following contact.

27. The kit according to claim 26, which additionally comprises a culture medium for the biological sample from said mammal to be detected.

28. The kit according to claim 26, in which the detection reagents are reagents to quantify IFN-γ secretion by ELISA or Elispot.

29. The kit according to claim 26, in which the detection reagents are reagents to quantify intracytoplasmic IFN-γ by flow cytometry.

* * * * *